(12) United States Patent
Abouabdellah et al.

(10) Patent No.: US 7,632,850 B2
(45) Date of Patent: Dec. 15, 2009

(54) ARYLALKYLCARBAMATE DERIVATIVES AND PRODUCTION THEREOF

(75) Inventors: Ahmed Abouabdellah, Thiais (FR);
Antonio Almario Garcia, Chatenay Malabry (FR); Christian Hoornaert, Antony (FR); Antoine Ravet, Rueil-Malmaison (FR)

(73) Assignee: Sanofi-aventis, Paris (FR)

( * ) Notice: Subject to any disclaimer, the term of this patent is extended or adjusted under 35 U.S.C. 154(b) by 614 days.

(21) Appl. No.: 11/186,242

(22) Filed: Jul. 21, 2005

(65) Prior Publication Data

US 2006/0014830 A1    Jan. 19, 2006

Related U.S. Application Data

(63) Continuation of application No. PCT/FR2004/000139, filed on Jan. 22, 2004.

(30) Foreign Application Priority Data

Jan. 23, 2003   (FR)   ................... 03 00704

(51) Int. Cl.
| | |
|---|---|
| *A61K 31/16* | (2006.01) |
| *A61K 31/165* | (2006.01) |
| *C07C 233/02* | (2006.01) |
| *C07C 237/00* | (2006.01) |
| *C07D 211/70* | (2006.01) |
| *C07D 213/18* | (2006.01) |
| *C07D 213/55* | (2006.01) |

(52) U.S. Cl. .................. 514/357; 514/613; 514/616; 514/617; 546/335; 564/123; 564/161; 564/164; 564/169; 564/193

(58) Field of Classification Search .............. 514/613, 514/616, 617; 546/335; 564/123, 161, 164, 564/169, 193
See application file for complete search history.

(56) References Cited

U.S. PATENT DOCUMENTS 6,462,054 B1    10/2002    Boger

FOREIGN PATENT DOCUMENTS

| WO | WO 02/087569 | 11/2002 |
|---|---|---|
| WO | WO 03/065989 | 8/2003 |

OTHER PUBLICATIONS

Morissette, et al (Advanced Drug Delivery Reviews, vol. 56, pp. 275-300; 2004).*
Vippagunta, et al (Advanced Drug Delivery Reviews, vol. 48, pp. 3-26; 2001).*
Giorgio Tarzia et al., Design, Synthesis, and Structure-Activity Relationships of Alkylcarbamic Acid Aryl Esters, a New Class of Fatty Acid Amide Hydrolase Inhibitors, J. Med Chem. (2003, pp. 2352-2360, vol. 46).
Dovlatyan, V., et al., Synthesis of Pesticides, XXVII, Intramolecular Cyclization of Alpha-Cynanoalkyl N-Arylcarbamates, Chemical Abstract, 14748u (1970) vol. 73, No. 3, pp. 358.

* cited by examiner

*Primary Examiner*—Phyllis G. Spivack
*Assistant Examiner*—Nelson C Blakely, III
(74) *Attorney, Agent, or Firm*—Balaram Gupta

(57) ABSTRACT

The present invention provides a compound of the formula (I):

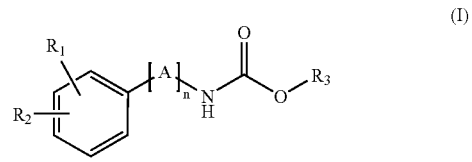

in which $R_1$, $R_2$, $R_3$, A and n are described and set forth more fully herein. Also provided are their preparation and their application in therapy.

9 Claims, No Drawings

ARYLALKYLCARBAMATE DERIVATIVES AND PRODUCTION THEREOF

This application is a continuation of International Application No. PCT/FR2004/000139, filed Jan. 22, 2004, which claims the benefit of priority of French Application No. 03/00704 filed Jan. 23, 2003.

The invention relates to arylalkylcarbamate derivatives, to their preparation and to their application in therapy.

The compounds of the invention are of the general formula (I):

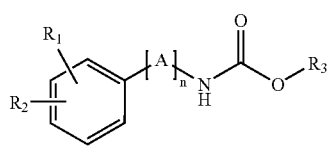

in which
n represents an integer ranging from 1 to 7;
A is selected from one or more groups X, Y and/or Z;
X represents a $C_{1-2}$-alkylene group optionally substituted by one or more $C_{1-12}$-alkyl, $C_{3-7}$-cycloalkyl or $C_{3-7}$-cycloalkyl-$C_{1-6}$-alkylene groups;
Y represents either a $C_2$-alkenylene group optionally substituted by one or more $C_{1-12}$-alkyl, $C_{3-7}$-cycloalkyl or $C_{3-7}$-cycloalkyl-$C_{1-6}$-alkylene groups; or a $C_2$-alkynylene group;
Z represents a $C_{3-7}$-cycloalkyl group of formula:

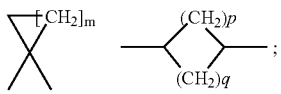

m represents an integer ranging from 1 to 5;
p and q represent integers and are defined such that p+q is a number ranging from 1 to 5;
$R_1$ represents a hydrogen or halogen atom or a hydroxy, cyano, nitro, $C_{1-4}$-alkyl, $C_{1-4}$-alkoxy, $C_{1-4}$-thioalkyl, $C_{1-4}$-fluoroalkyl, $C_{1-4}$-fluoroalkoxy or $C_{1-4}$-fluorothioalkyl group;
$R_2$ represents
a hydrogen or halogen atom or
a cyano, nitro, hydroxy, $C_{1-4}$-alkyl, $C_{1-4}$-alkoxy, $C_{1-4}$-thioalkyl, $C_{1-4}$-fluoroalkyl, $C_{1-4}$-fluoroalkoxy, $C_{1-4}$-fluorothioalkyl group, or
a group selected from in particular a phenyl, naphthyl, biphenyl, phenylethylenyl, naphthylethylenyl, pyridinyl, pyrimidinyl, pyrazinyl, pyridazinyl, triazinyl, indanyl, indenyl, quinolinyl, isoquinolinyl, quinazolinyl, quinoxalinyl, phthalazinyl, cinnolinyl, thienyl, furanyl, pyrrolyl, imidazolyl, pyrazolyl, oxazolyl, thiazolyl, isoxazolyl, isothiazolyl, thiadiazolyl, oxadiazolyl, triazolyl, phenylimidazolyl, benzothienyl, benzofuranyl, dibenzofuranyl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsulphonyl, benzoyl, benzyloxy, phenylethoxy, phenylpropoxy, naphthyloxy, naphthylmethoxy, naphthylethoxy, naphthylpropoxy, quinolinoxy and isoquinolinoxy and optionally substituted by one or more substituents selected from a halogen atom or a cyano, nitro, $C_{1-4}$-alkyl, hydroxy, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidinyl, pyrrolidinyl, morpholinyl, $NR_6R_7$, $NHCOR_6$, $COR_6$, $CO_2R_6$, $SO_2R_6$, —O—($C_{1-3}$-alkylene)-O— or 4-piperazinyl group optionally substituted by a $C_{1-3}$-alkyl or by a benzyl;
$R_6$ and $R_7$ represent independently of one another a $C_{1-3}$-alkyl group or a phenyl; and
$R_3$ represents a group of general formula $CHR_4CONHR_5$ in which
$R_4$ represents a hydrogen atom or a $C_{1-3}$-alkyl group and
$R_5$ represents a hydrogen atom or a $C_{1-3}$-alkyl, $C_{3-5}$-cycloalkyl or $C_{3-7}$-cycloalkyl-$C_{1-6}$-alkylene group.

In the entire text of the patent application, the following compound does not form part of the invention:
2-amino-2-oxoethyl benzylcarbamate.

In the context of the invention the compounds of general formula (I) may therefore contain two or more identical or different groups A.

Among the compounds of general formula (I) a first class of preferred compounds is composed of compounds for which:
n represents an integer ranging from 1 to 7;
A is selected from one or more groups X, Y and/or Z;
X represents a $C_{1-2}$-alkylene group optionally substituted by one or more $C_{1-12}$-alkyl, $C_{3-7}$-cycloalkyl or $C_{3-7}$-cycloalkyl-$C_{1-6}$-alkylene groups;
Y represents either a $C_2$-alkenylene group optionally substituted by one or more $C_{1-12}$-alkyl, $C_{3-7}$-cycloalkyl or $C_{3-7}$-cycloalkyl-$C_{1-6}$-alkylene groups; or a $C_2$-alkynylene group;
Z represents a $C_{3-7}$-cycloalkyl group of formula:

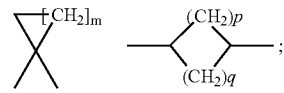

m represents an integer ranging from 1 to 5;
p and q represent integers and are defined such that p+q is a number ranging from 1 to 5;
$R_1$ represents a hydrogen or halogen atom or a hydroxy, cyano, nitro, $C_{1-4}$-alkyl, $C_{1-4}$-alkoxy, $C_{1-4}$-thioalkyl, $C_{1-4}$-fluoroalkyl, $C_{1-4}$-fluoroalkoxy or $C_{1-4}$-fluorothioalkyl group;
$R_2$ represents
a hydrogen or halogen atom or
a cyano, nitro, hydroxy, $C_{1-4}$-alkyl, $C_{1-4}$-alkoxy, $C_{1-4}$-thioalkyl, $C_{1-4}$-fluoroalkyl, $C_{1-4}$-fluoroalkoxy, $C_{1-4}$-fluorothioalkyl group, or
a group selected from in particular a phenyl, naphthyl, biphenyl, phenylethylenyl, naphthylethylenyl, pyridinyl, pyrimidinyl, pyrazinyl, pyridazinyl, triazinyl, indanyl, indenyl, quinolinyl, isoquinolinyl, quinazolinyl, quinoxalinyl, phthalazinyl, cinnolinyl, thienyl, furanyl, pyrrolyl, imidazolyl, pyrazolyl, oxazolyl, thiazolyl, isoxazolyl, isothiazolyl, thiadiazolyl, oxadiazolyl, triazolyl, phenylimidazolyl, benzothienyl, benzofuranyl, dibenzofuranyl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsulphonyl, benzoyl, benzyloxy, phenylethoxy, phenylpropoxy, naphthyloxy, naphthylmethoxy, naphthylethoxy, naphthylpropoxy, quinolinoxy and isoquinolinoxy and optionally substituted by one or more substituents selected from a halogen atom and a cyano, nitro, $C_{1-4}$-alkyl, hydroxy, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidinyl, pyrrolidinyl, morpholinyl, $NR_6R_7$, $NHCOR_6$, $COR_6$, $CO_2R_6$, $SO_2R_6$, —O—($C_{1-3}$-alkylene)-O— or 4-piperazinyl group optionally substituted by a $C_{1-3}$-alkyl or by a benzyl;

$R_6$ and $R_7$ represent independently of one another a $C_{1-3}$-alkyl group or a phenyl; and $R_3$ represents a group of general formula $CHR_4CONHR_5$ in which $R_4$ represents a hydrogen atom or a $C_{1-3}$-alkyl group and $R_5$ represents a hydrogen atom or a $C_{1-3}$-alkyl, $C_{3-5}$-cycloalkyl or $C_{3-7}$-cycloalkyl-$C_{1-6}$-alkylene group;

with the proviso that if $R_1$ and $R_2$ represent a hydrogen atom and A is a group X, X being a methylene, then n is other than 1.

Among the compounds of general formula (I) a second class of preferred compounds is composed of compounds for which:

when n is 1:

A is selected from one or more groups X, Y and/or Z;

X represents a $C_{1-2}$-alkylene group optionally substituted by one or more $C_{1-12}$-alkyl, $C_{3-7}$-cycloalkyl or $C_{3-7}$-cycloalkyl-$C_{1-6}$-alkylene groups;

Y represents either a $C_2$-alkenylene group optionally substituted by one or more $C_{1-12}$-alkyl, $C_{3-7}$-cycloalkyl or $C_{3-7}$-cycloalkyl-$C_{1-6}$-alkylene groups or a $C_2$-alkynylene group;

z represents a $C_{3-7}$-cycloalkyl group of formula:

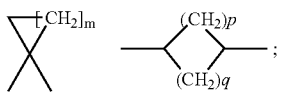

m represents an integer ranging from 1 to 5;

p and q represent integers and are defined such that p+q is a number ranging from 1 to 5;

$R_1$ represents a hydrogen or halogen atom or a hydroxy, cyano, nitro, $C_{1-4}$-alkyl, $C_{1-4}$-alkoxy, $C_{1-4}$-thioalkyl, $C_{1-4}$-fluoroalkyl, $C_{1-4}$-fluoroalkoxy or $C_{1-4}$-fluorothioalkyl group;

$R_2$ represents a halogen atom or a cyano, nitro, hydroxy, $C_{1-4}$-alkyl, $C_{1-4}$-alkoxy, $C_{1-4}$-thioalkyl, $C_{1-4}$-fluoroalkyl, $C_{1-4}$-fluoroalkoxy, $C_{1-4}$-fluorothioalkyl group, or a group selected from in particular a phenyl, naphthyl, biphenyl, phenylethylenyl, naphthylethylenyl, pyridinyl, pyrimidinyl, pyrazinyl, pyridazinyl, triazinyl, indanyl, indenyl, quinolinyl, isoquinolinyl, quinazolinyl, quinoxalinyl, phthalazinyl, cinnolinyl, thienyl, furanyl, pyrrolyl, imidazolyl, pyrazolyl, oxazolyl, thiazolyl, isoxazolyl, isothiazolyl, thiadiazolyl, oxadiazolyl, triazolyl, phenylimidazolyl, benzothienyl, benzofuranyl, dibenzofuranyl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsulphonyl, benzoyl, benzyloxy, phenylethoxy, phenylpropoxy, naphthyloxy, naphthylmethoxy, naphthylethoxy, naphthylpropoxy, quinolinoxy and isoquinolinoxy and optionally substituted by one or more substituents selected from a halogen atom and a cyano, nitro, $C_{1-4}$-alkyl, hydroxy, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidinyl, pyrrolidinyl, morpholinyl, $NR_6R_7$, $NHCOR_6$, $COR_6$, $CO_2R_6$, $SO_2R_6$, —O—($C_{1-3}$-alkylene)-O— or 4-piperazinyl group optionally substituted by a $C_{1-3}$-alkyl or by a benzyl;

$R_6$ and $R_7$ represent independently of one another a $C_{1-3}$-alkyl group or a phenyl; and $R_3$ represents a group of general formula $CHR_4CONHR_5$ in which $R_4$ represents a hydrogen atom or a $C_{1-3}$-alkyl group and $R_5$ represents a hydrogen atom or a $C_{1-3}$-alkyl, $C_{3-5}$-cycloalkyl or $C_{3-7}$-cycloalkyl-$C_{1-6}$-alkylene group;

when n represents an integer ranging from 2 to 7:

A is selected from one or more groups X, Y and/or Z;

X represents a $C_{1-2}$-alkylene group optionally substituted by one or more $C_{1-12}$-alkyl, $C_{3-7}$-cycloalkyl or $C_{3-7}$-cycloalkyl-$C_{1-6}$-alkylene groups;

Y represents either a $C_2$-alkenylene group optionally substituted by one or more $C_{1-12}$-alkyl, $C_{3-7}$-cycloalkyl or $C_{3-7}$-cycloalkyl-$C_{1-6}$-alkylene groups; or a $C_2$-alkynylene group;

Z represents a $C_{3-7}$-cycloalkyl group of formula:

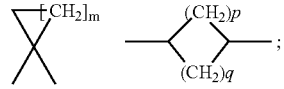

m represents an integer ranging from 1 to 5;

p and q represent integers and are defined such that p+q is a number ranging from 1 to 5;

$R_1$ represents a hydrogen or halogen atom or a hydroxy, cyano, nitro, $C_{1-4}$-alkyl, $C_{1-4}$-alkoxy, $C_{1-4}$-thioalkyl, $C_{1-4}$-fluoroalkyl, $C_{1-4}$-fluoroalkoxy or $C_{1-4}$-fluorothioalkyl group;

$R_2$ represents a hydrogen or halogen atom or a cyano, nitro, hydroxy, $C_{1-4}$-alkyl, $C_{1-4}$-alkoxy, $C_{1-4}$-thioalkyl, $C_{1-4}$-fluoroalkyl, $C_{1-4}$-fluoroalkoxy, $C_{1-4}$-fluorothioalkyl group, or a group selected from in particular a phenyl, naphthyl, biphenyl, phenylethylenyl, naphthylethylenyl, pyridinyl, pyrimidinyl, pyrazinyl, pyridazinyl, triazinyl, indanyl, indenyl, quinolinyl, isoquinolinyl, quinazolinyl, quinoxalinyl, phthalazinyl, cinnolinyl, thienyl, furanyl, pyrrolyl, imidazolyl, pyrazolyl, oxazolyl, thiazolyl, isoxazolyl, isothiazolyl, thiadiazolyl, oxadiazolyl, triazolyl, phenylimidazolyl, benzothienyl, benzofuranyl, dibenzofuranyl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsulphonyl, benzoyl, benzyloxy, phenylethoxy, phenylpropoxy, naphthyloxy, naphthylmethoxy, naphthylethoxy, naphthylpropoxy, quinolinoxy and isoquinolinoxy and optionally substituted by one or more substituents selected from a halogen atom and a cyano, nitro, $C_{1-4}$-alkyl, hydroxy, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidinyl, pyrrolidinyl, morpholinyl, $NR_6R_7$, $NHCOR_6$, $COR_6$, $CO_2R_6$, $SO_2R_6$, —O—($C_{1-3}$-alkylene)-O— or 4-piperazinyl group optionally substituted by a $C_{1-3}$-alkyl or by a benzyl;

$R_6$ and $R_7$ represent independently of one another a $C_{1-3}$-alkyl group or a phenyl; and $R_3$ represents a group of general formula $CHR_4CONHR_5$ in which $R_4$ represents a hydrogen atom or a $C_{1-3}$-alkyl group and $R_5$ represents a hydrogen atom or a $C_{1-3}$-alkyl, $C_{3-5}$-cycloalkyl or $C_{3-7}$-cycloalkyl-$C_{1-6}$-alkylene group.

Among the compounds of general formula (I) a third class of particularly preferred compounds is composed of the compounds for which:

n represents an integer between 1 and 5; and/or

A is selected from one or more groups X and/or Z;

X represents a $C_{1-2}$-alkylene group, more particularly methylene, optionally substituted by one or more $C_{1-3}$-alkyl groups, more particularly methyl;

z represents a $C_{3-7}$-cycloalkyl group of formula:

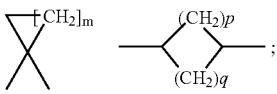

m represents an integer ranging from 1 to 5, more particularly 1;

p and q represent integers and are defined such that p+q is a number ranging from 1 to 5, more particularly 4; and/or $R_1$ represents a hydrogen or a halogen, more particularly chlorine or fluorine, or a $C_{1-4}$-alkoxy group, more particularly a methoxy; and/or $R_2$ represents a hydrogen or halogen atom, more particularly chlorine, bromine or fluorine, or a hydroxyl group, $C_{1-4}$-alkyl group, more particularly methyl, $C_{1-4}$-alkoxy group, more particularly methoxy, $C_{1-4}$-fluoroalkyl group, more particularly trifluoromethyl, or $C_{1-4}$-fluoroalkoxy group, more particularly trifluoromethoxy, or a group selected from phenyl, naphthyl, biphenylyl, phenylethylenyl, pyridinyl, pyrimidinyl, pyrazinyl, quinolinyl, isoquinolinyl, thienyl, furanyl, isoxazolyl, thiadiazolyl, phenylimidazolyl, benzothienyl, dibenzofuranyl, benzimidazolyl, pyrrolopyridinyl, phenyloxy, phenylsulphonyl, benzoyl, benzyloxy or phenylpropoxy, optionally substituted by one or more substituents selected from a halogen atom, more particularly chlorine or fluorine, or a cyano, nitro or $C_{1-4}$-alkyl group, more particularly methyl, ethyl, isopropyl, butyl or tert-butyl, $C_{1-6}$-alkoxy group, more particularly methoxy or ethoxy, $C_{1-4}$-thioalkyl group, more particularly thiomethyl, $C_{1-3}$-fluoroalkyl group, more particularly trifluoromethyl, $C_{1-3}$-fluoroalkoxy group, more particularly trifluoromethoxy, phenyloxy, or benzyloxy, $NR_6R_7$, $NHCOR_6$, $COR_6$, $CO_2R_6$, $SO_2R_6$ or —O—($C_{1-3}$-alkylene)-O—, more particularly —O—($CH_2$)—O—; and/or $R_6$ and $R_7$ represent independently of one another a $C_{1-3}$-alkyl group, more particularly a methyl; and/or $R_3$ represents a group of general formula $CHR_4CONHR_5$ in which $R_4$ represents a hydrogen atom or a $C_{1-3}$-alkyl group and $R_5$ represents a hydrogen atom or a $C_{1-3}$-alkyl group, more particularly methyl, ethyl, $C_{3-5}$-cycloalkyl, more particularly cyclopropyl, or $C_{3-7}$-cycloalkyl-$C_{1-6}$-alkylene, more particularly cyclopropylmethyl.

Among the compounds of this third class of particularly preferred compounds more particular preference is given to the compounds for which:

n represents an integer from 1 to 5; and/or

A represents a $C_{1-2}$-alkylene group, more particularly methylene; and/or $R_1$ represents a hydrogen or a halogen, more particularly chlorine or fluorine; and/or $R_2$ represents a group selected from phenyl, naphthyl, phenyloxy, benzyloxy, pyridinyl, quinolinyl, isoquinolinyl, phenylimidazole or pyrrolopyridinyl, optionally substituted by one or more substituents selected from a halogen atom, more particularly chlorine or fluorine, a cyano group, a $C_{1-4}$-alkyl group, more particularly methyl, $C_{1-4}$-alkoxy group, more particularly methoxy, $C_{1-3}$-fluoroalkyl group, more particularly trifluoromethyl, $C_{1-3}$-fluoroalkoxy group, more particularly trifluoromethoxy; and/or $R_3$ represents a group of general formula $CHR_4CONHR_5$ in which $R_4$ represents a hydrogen and $R_5$ represents a hydrogen atom or a $C_{1-3}$-alkyl group, more particularly methyl or ethyl, $C_{3-5}$-cycloalkyl group, more particularly cyclopropyl, or $C_{3-7}$-cycloalkyl-$C_{1-6}$-alkylene group, more particularly cyclopropylmethyl.

Among the compounds of general formula (I) a fourth class of particularly preferred compounds is composed of compounds for which:

n represents an integer from 5 to 7; and/or

A represents a $C_{1-2}$-alkylene group, more particularly methylene; and/or $R_1$ and $R_2$ represent independently of one another a hydrogen or halogen atom or a cyano, hydroxyl, $C_{1-4}$-alkyl, $C_{1-4}$-alkoxy, $C_{1-4}$-fluoroalkyl or $C_{1-4}$-fluoroalkoxy group; and/or $R_3$ represents a group of general formula $CHR_4CONHR_5$ in which $R_4$ represents a hydrogen and $R_5$ represents a hydrogen atom or $C_{1-3}$-alkyl group, more particularly methyl or ethyl, $C_{3-5}$-cycloalkyl group, more particularly cyclopropyl, or $C_{3-7}$-cycloalkyl-$C_{1-6}$-alkylene group, more particularly cyclopropylmethyl.

The invention also relates, among the compounds of general formula (I), to compounds of the general formula (I'):

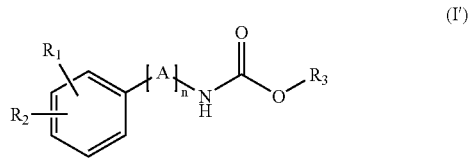

in which n represents an integer between 1 and 6;

A is selected from one or more groups X, Y and/or Z;

X represents a $C_{1-2}$-alkylene group optionally substituted by one or more $C_{1-12}$-alkyl, $C_{3-7}$-cycloalkyl or $C_{3-7}$-cycloalkyl-$C_{1-6}$-alkylene groups;

Y represents a $C_2$-alkenylene group optionally substituted by one or more $C_{1-12}$-alkyl, $C_{3-7}$-cycloalkyl or $C_{3-7}$-cycloalkyl-$C_{1-6}$-alkylene groups;

Z represents a $C_{3-7}$-cycloalkyl group of formula:

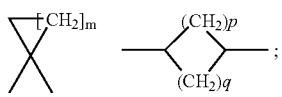

m represents an integer ranging from 1 to 5;
p and q represent integers and are defined such that p+q is a number ranging from 1 to 5;
$R_1$ represents a hydrogen or halogen atom or a hydroxy, cyano, nitro, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group;
$R_2$ represents
a hydrogen or halogen atom or
a cyano, nitro, hydroxy, $C_{1-3}$-alkyl, $C_{1-3}$-alkoxy, $C_{1-3}$-thioalkyl, $C_{1-3}$-fluoroalkyl, $C_{1-3}$-fluoroalkoxy, $C_{1-3}$-fluorothioalkyl group, or
a group selected from a phenyl, naphthyl, biphenyl, phenylethylenyl, naphthylethylenyl, pyridinyl, pyrimidinyl, pyrazinyl, pyridazinyl, triazinyl, indanyl, indenyl, quinolinyl, isoquinolinyl, quinazolinyl, quinoxalinyl, phthalazinyl, cinnolinyl, thienyl, furanyl, pyrrolyl, imidazolyl, pyrazolyl, oxazolyl, thiazolyl, isoxazolyl, isothiazolyl, thiadiazolyl, oxadiazolyl, triazolyl, benzothienyl, benzofuranyl, dibenzofuranyl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsulphonyl, benzoyl, benzyloxy, phenylethoxy, phenylpropoxy, naphthyloxy, naphthylmethoxy, naphthylethoxy, naphthylpropoxy, quinolinoxy and isoquinolinoxy and optionally substituted by one or more substituents selected from a halogen atom and a cyano, nitro, $C_{1-4}$-alkyl, hydroxy, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidinyl, pyrrolidinyl, morpholinyl, $NR_6R_7$, $NHCOR_6$, $COR_6$, $CO_2R_6$, $SO_2R_6$, —O—($C_{1-3}$-alkylene)-O— or 4-piperazinyl group optionally substituted by a $C_{1-3}$-alkyl or by a benzyl;
$R_6$ and $R_7$ represent independently of one another a $C_{1-3}$-alkyl group or a phenyl; and
$R_3$ represents a group of general formula $CHR_4CONHR_5$ in which
$R_4$ represents a hydrogen atom or a $C_{1-3}$-alkyl group and $R_5$ represents a hydrogen atom or a $C_{1-3}$-alkyl, $C_{3-5}$-cycloalkyl or $C_{3-7}$-cycloalkyl-$C_{1-6}$-alkylene group.

The compounds of general formula (I) may include one or more asymmetric carbons. They may exist in the form of enantiomers or diastereoisomers. These enantiomers and diastereoisomers, and their mixtures, including the racemic mixtures, form part of the invention.

The compounds of formula (I) may exist in the form of bases or of addition salts with acids. Such addition salts form part of the invention.

These salts are advantageously prepared with pharmaceutically acceptable acids, although the salts of other acids which are of use, for example, for purifying or isolating the compounds of formula (I) also form part of the invention.

The compounds of general formula (I) may be in the form of hydrates or solvates, namely in the form of associations or combinations with one or more molecules of water or with a solvent. Such hydrates and solvates also form part of the invention.

In the context of the invention the terms are understood as follows:
$C_{t-z}$, where t and z can take the values from 1 to 12, is a carbon chain which can have from t to z carbon atoms; for example, $C_{1-3}$ is a carbon chain which can have from 1 to 3 carbon atoms;
alkyl is a saturated, linear or branched aliphatic group; for example, a $C_{1-3}$-alkyl group represents a linear or branched carbon chain of from 1 to 3 carbon atoms, more particularly a methyl, ethyl, propyl or 1-methylethyl;
alkylene is a saturated, linear or branched divalent alkyl group; for example, a $C_{1-3}$-alkylene group represents a linear or branched divalent carbon chain of from 1 to 3 carbon atoms, more particularly a methylene, ethylene, 1-methylethylene or propylene;
cycloalkyl is a cyclic alkyl group; for example, a $C_{3-5}$-cycloalkyl group represents a cyclic carbon group of from 3 to 5 carbon atoms, more particularly a cyclopropyl, cyclobutyl or cyclopentyl;
alkenylene is a divalent unsaturated aliphatic group of two carbons, more particularly an ethylene;
$C_2$-alkynylene is a —C≡C— group;
alkoxy is an —O-alkyl group with a saturated, linear or branched aliphatic chain;
thioalkyl is an S-alkyl group with a saturated, linear or branched aliphatic chain;
fluoroalkyl is an alkyl group in which one or more hydrogen atoms have been substituted by a fluorine atom;
fluoroalkoxy is an alkoxy group in which one or more hydrogen atoms have been substituted by a fluorine atom;
fluorothioalkyl is a thioalkyl group in which one or more hydrogen atoms have been substituted by a fluorine atom; and
a halogen atom is a fluorine, a chlorine, a bromine or an iodine.

The compounds of the invention may be prepared according to a variety of methods, which are illustrated by the schemes which follow.

Thus a first method (scheme 1) consists in reacting an amine of general formula (II), in which $R_1$, $R_2$, n and A are as defined above, with a carbonate of general formula (III), in which U represents a hydrogen atom or a nitro group and $R_3$ is as defined above, in a solvent such as toluene or dichloroethane at a temperature of between 0 and 80° C.

Scheme 1

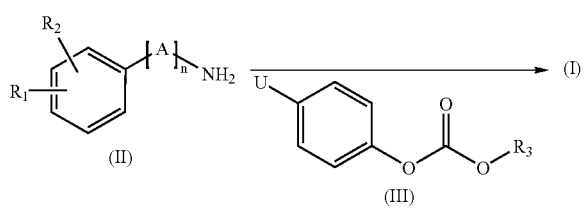

The carbonates of general formula (III) may be prepared according to any method described in the literature; for example, by reacting an alcohol of general formula $HOR_3$ with phenyl chloroformate or 4-nitrophenyl chloroformate in the presence of a base such as triethylamine or diisopropylethylamine.

Another method (scheme 2) of obtaining compounds of general formula (I) consists in reacting an amine of general formula (II), as defined above, with a carbonate of general formula (IIIa), in which V represents a hydrogen atom or a nitro group, $R_4$ is as defined above and R represents a methyl or ethyl group. The carbamate ester of general formula (Ia) thus obtained is subsequently converted into a compound of general formula (I) by aminolysis using an amine of general formula $R_5NH_2$, in which $R_5$ is as defined above. The aminolysis reaction may be conducted in a solvent such as methanol or a mixture of solvents such as methanol and tetrahydrofuran.

The carbonates of general formula (IIIa) may be prepared similarly to the carbonates of formula (III).

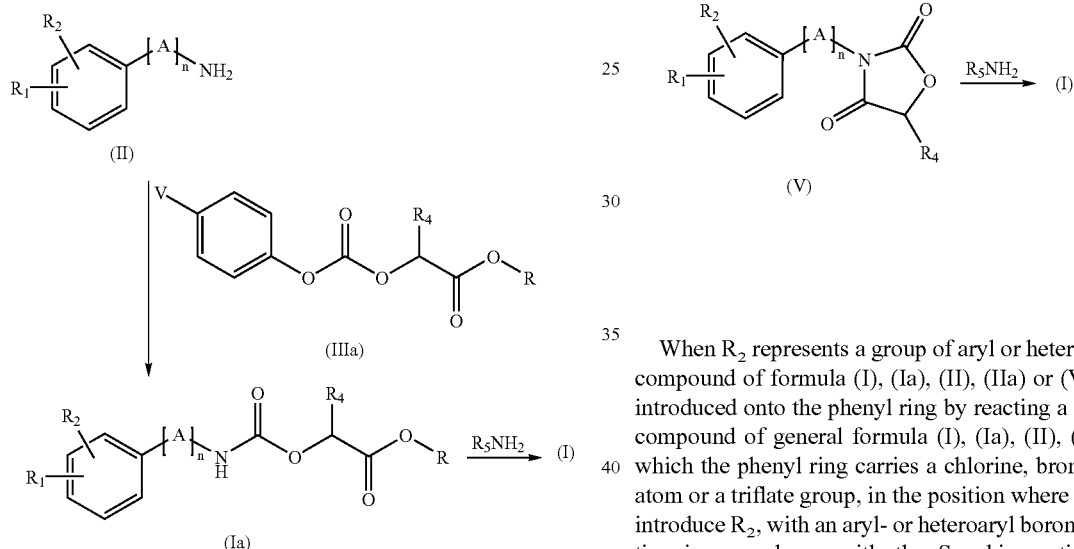

A variant preparation (scheme 3) of the compounds of general formula (I) consists in reacting a derivative of general formula (IIa), in which $R_1$, $R_2$, n and A are as defined above and W represents a hydroxy, mesylate or tosylate group, or a chlorine, bromine or iodine atom, with an oxazolidinedione of general structure (IV), in which $R_4$ is as defined above, to give the oxazolidinedione derivative of general structure (V).

Where W represents a hydroxy group the reaction may be performed in accordance with the Mitsunobu conditions (Synthesis 1981, 1-28), for example, by the action of diethyl or diisopropyl azodicarboxylate in the presence of triphenylphosphine. Where X represents a chlorine, bromine or iodine atom or a mesylate or tosylate group the reaction may be performed in the presence of a base such as 1,1,3,3-tetramethylguanidine, sodium hydride or sodium tert-butoxide in a solvent such as tetrahydrofuran, acetonitrile or dimethylformamide at a temperature of between 0° C. and 80° C. The oxazolidinedione derivative of general formula (V) thus obtained is subsequently converted into a compound of general formula (I) by aminolysis using an amine of general formula $R_5NH_2$, in which $R_5$ is as defined above.

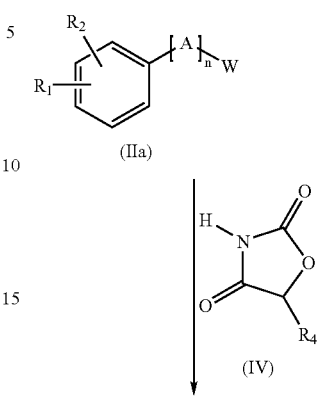

When $R_2$ represents a group of aryl or heteroaryl type in a compound of formula (I), (Ia), (II), (IIa) or (V), $R_2$ may be introduced onto the phenyl ring by reacting a derivative of a compound of general formula (I), (Ia), (II), (IIa) or (V) in which the phenyl ring carries a chlorine, bromine or iodine atom or a triflate group, in the position where it is desired to introduce $R_2$, with an aryl- or heteroaryl boronic acid derivative in accordance with the Suzuki reaction conditions (*Chem. Rev.* (1995), 95, 2457-2483), or with an aryl or heteroaryl trialkyltin derivative in accordance with the Stille reaction conditions (*Angew. Chem.* (1986), 25, 508-524).

When $R_2$ represents an aryloxy or imidazolyl, pyrrolopyridinyl or indolyl group in a compound of formula (I), (Ia), (II), (IIa) or (V), the introduction of $R_2$ onto the phenyl ring can be carried out by an O-arylation or N-arylation reaction in accordance with the Buchwald reaction conditions (*Angew. Chem.* (2003), 42, 5400-5449).

The compounds of general formulae (II), (IIa) and (IV), when the method by which they are prepared is not described, are available commercially or described in the literature, or else may be prepared according to methods which are described therein or which are known to the person skilled in the art.

The compounds of general formula (Ia) in which n, A, $R_1$, $R_2$ and $R_4$ are as defined for the general formula (I) and R represents a methyl or ethyl group are novel and also form part of the invention. They are useful as synthesis intermediates for the preparation of the compounds of general formula (I).

The compounds of general formula (V) in which n, A, $R_1$ and $R_4$ are as defined for the general formula (I) and where $R_2$ represents a hydrogen, bromine, iodine or fluorine atom or a cyano, nitro, hydroxy, $C_{1-4}$-alkyl, $C_{1-4}$-alkoxy, $C_{1-4}$-thioalkyl, $C_{1-4}$-fluoroalkyl, $C_{1-4}$-fluoroalkoxy or $C_{1-4}$-fluorothioalkyl group, or a group selected from a phenyl, naphthyl, biphenyl, phenylethylenyl, naphthylethylenyl, pyridinyl, pyrimidinyl, pyrazinyl, pyridazinyl, triazinyl, indanyl, indenyl, quinolinyl, isoquinolinyl, quinazolinyl, quinoxalinyl, phthalazinyl, cinnolinyl, thienyl, furanyl, pyrrolyl, imidazolyl, pyrazolyl, oxazolyl, thiazolyl, isoxazolyl, isothiazolyl, thiadiazolyl, oxadiazolyl, triazolyl, phenylimidazolyl, benzothienyl, benzofuranyl, dibenzofuranyl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsulphonyl, benzoyl, benzyloxy, phenylethoxy, phenylpropoxy, naphthyloxy, naphthylmethoxy, naphthylethoxy, naphthylpropoxy, quinolinoxy and isoquinolinoxy and optionally substituted by one or more substituents selected from a halogen atom and a cyano, nitro, $C_{1-4}$-alkyl, hydroxy, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidinyl, pyrrolidinyl, morpholinyl, $NR_6R_7$, $NHCOR_6$, $COR_6$, $CO_2R_6$, $SO_2R_6$, —O—($C_{1-3}$-alkylene)-O— or 4-piperazinyl group optionally substituted by a $C_{1-3}$-alkyl or by a benzyl; and $R_6$ and $R_7$ represent independently of one another a $C_{1-3}$-alkyl group or a phenyl; are novel and also form part of the invention. They are useful as synthesis intermediates for the preparation of the compounds of general formula (I).

The examples which now follow illustrate the preparation of some compounds of the invention. These examples are not limited to this and merely illustrate the invention. The microanalyses, IR and NMR spectra and/or the LC-MS (liquid chromatography coupled to mass spectroscopy) confirm the structures and purities of the compounds obtained.

m.p. (° C.) represents the melting point in degrees Celsius.

The numbers indicated between brackets in the titles of the examples correspond to those of the 1st column of the table hereinafter.

IUPAC (International Union of Pure and Applied Chemistry) nomenclature has been used to name the compounds in the following examples. For example, for the biphenyl group, the following numbering has been respected:

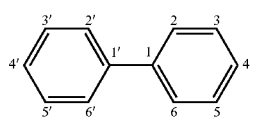

EXAMPLE 1

Compound 1

2-(methylamino)-2-oxoethyl 1,1'-biphenyl-4-ylmethylcarbamate

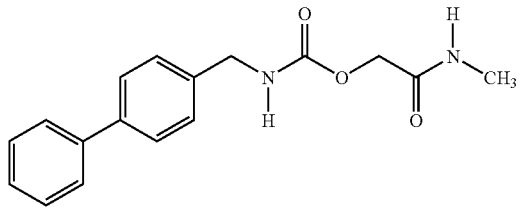

0.1 g (0.97 mmol) of N-methyl-2-hydroxyacetamide is admixed dropwise at ambient temperature with a solution of 0.196 g (0.97 mmol) of 4-nitrophenyl chloroformate in 3 ml of methylene chloride and 0.166 ml (0.97 mmol) of N,N-diisopropylethylamine. The mixture is stirred at ambient temperature for 45 minutes and then a solution of 0.195 g (1.067 mmol) of 4-phenylbenzylamine in 3 ml of methylene chloride and 0.166 ml (0.97 mmol) of N,N-diisopropylethylamine is added dropwise at ambient temperature. The mixture is stirred at ambient temperature for 1 hour. It is washed with saturated aqueous ammonium chloride solution, with aqueous 10% sodium carbonate solution and with saturated aqueous sodium chloride solution. The phases are separated and the organic phase is dried over sodium sulphate. The system is filtered, the filtrate is concentrated under reduced pressure and the residue is purified by chromatography on silica gel using ethyl acetate.

This gives 0.1 g of white solid.
LC-MS: M+H=299
m.p. (° C.): 189-190° C.
$^1$H NMR (DMSO-$d_6$) δ (ppm): 7.90-7.35 (m, 11H); 4.40 (s, 2H); 4.30 (d, 2H); 2.65 (d, 3H).

EXAMPLE 2

Compound 125

2-(methylamino)-2-oxoethyl 2-[4-(trifluoromethyl)phenyl]ethylcarbamate

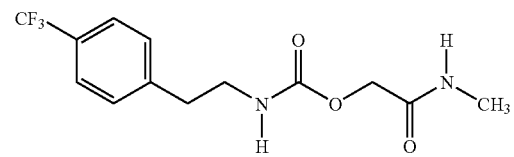

2.1. 3-{2-[4-(trifluoromethyl)phenyl]ethyl}-1,3-oxazolidine-2,4-dione

A solution of 1.4 g (7.36 mmol) of 2-[4-(trifluoromethyl)phenyl]ethanol, 2.22 g (8.47 mmol) of triphenylphosphine and 0.82 g (8.1 mmol) of 1,3-oxazolidine-2,4-dione (J. Med. Chem. 1991, 34, 1542-1543) in 25 ml of tetrahydrofuran, cooled to approximately −10° C., is admixed dropwise under an inert atmosphere with a solution of 1.7 g (8.47 mmol) of diisopropyl azodicarboxylate (DIAD) in 5 ml of tetrahydrofuran, while maintaining the temperature of the reaction mixture between −10° C. and 0° C. Stirring is continued at 0° C. for 1 hour and then at 25° C. for 20 hours.

The filtrate is concentrated under reduced pressure and the residue is taken up in dichloromethane and aqueous 5% sodium hydroxide solution (10 ml). The aqueous phase is separated and then extracted twice with dichloromethane. The organic phases are combined and washed in succession with aqueous hydrochloric acid solution (1N) and then saturated aqueous sodium hydrogencarbonate solution and saturated aqueous sodium chloride solution. The organic phase is dried over sodium sulphate and the filtrate is concentrated under reduced pressure. The residue thus obtained is purified by chromatography on silica gel, eluting with a 20/80 mixture of ethyl acetate and cyclohexane.

This gives 1.5 g of oxazolidinedione in the form of an oil.

2.2. 2-(methylamino)-2-oxoethyl 2-[4-(trifluoromethyl)phenyl]ethylcarbamate

A solution of 0.75 g (2.74 mmol) of 3-{2-[4-(trifluoromethyl)phenyl]ethyl}-1,3-oxazolidine-2,4-dione obtained in step 2.1., in 10 ml of methanol is admixed with 8 ml (16.47 mmol) of a solution (2M) of methylamine in tetrahydrofuran. Stirring is continued at ambient temperature for 12 hours.

Following concentration under reduced pressure the residue obtained is purified by chromatography on silica gel, eluting with a 95/5 mixture of dichloromethane and methanol. A white solid is obtained which is recrystallized from a mixture of ethyl acetate and diisopropyl ether.

This gives 0.530 g of pure product.
LC-MS: M+H=305
m.p. (° C.): 140-142° C.
$^1$H NMR (CDCl$_3$) δ (ppm): 2.85 (d, 3H); 2.95 (t, 2H); 3.50 (q, 2H); 4.60 (s, 2H); 4.90 (broad s, 1H); 6.15 (broad s, 1H); 7.35 (d, 2H); 7.60 (d, 2H).

EXAMPLE 3

Compound 150

2-(methylamino)-2-oxoethyl 2-(4'-chloro-1,1'-biphenyl-4-yl)ethylcarbamate

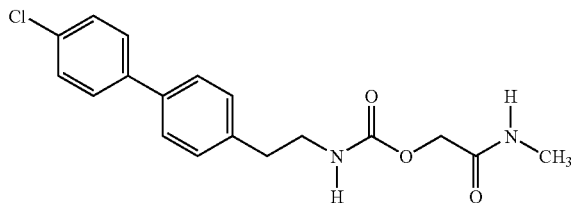

3.1. 3-[2-(4-bromophenyl)ethyl]-1,3-oxazolidine-2,4-dione

The procedure described in Example 2 (step 2.1.) is used; starting from 4 g (19.89 mmol) of 2-(4-bromophenyl)ethanol, 6.3 g (23.87 mmol) of triphenylphosphine, 2.4 g (23.87 mmol) of 1,3-oxazolidine-2,4-dione and 4.8 g (23.87 mmol) of diisopropyl azodicarboxylate, 4.6 g of pure product are obtained in the form of a white solid, after chromatography on silica gel, eluting with dichloromethane.
m.p. (° C.): 122-124° C.

3.2. 3-[2-(4'-chloro-1,1'-biphenyl-4-yl)ethyl]-1,3-oxazolidine-2,4-dione

A 250 ml three-necked round-bottomed flask placed under an inert atmosphere is charged with 2 g (7.04 mmol) of 3-[2-(4-bromophenyl)ethyl]-1,3-oxazolidine-2,4-dione, obtained in step 3.1., 2.2 g (14.08 mmol) of 4-chlorophenylboronic acid and 6.5 g (28.16 mmol) of potassium phosphate hydrate in suspension in 100 ml of 1,2-dimethoxyethane. Subsequently 0.80 g (0.70 mmol) of palladium tetrakis(triphenylphosphine) is added. The reaction mixture is subsequently refluxed overnight. The salts are separated by filtration over Celite and then the filtrate is concentrated under reduced pressure. The residue is taken up in ethyl acetate and water. The organic phase is separated and is washed with saturated aqueous sodium chloride solution. The filtrate is concentrated under reduced pressure and the residue is purified by chromatography on silica gel, eluting with dichloromethane.

This gives 1.22 g of pure product in the form of a white solid.
m.p. (° C.): 182-184° C.

3.3. 2-(methylamino)-2-oxoethyl 2-(4'-chloro-1,1'-biphenyl-4-yl)ethylcarbamate The procedure described in Example 2 (step 2.2.) is repeated. Starting from 0.40 g (1.27 mmol) of 3-[2-(4'-chloro-1,1'-biphenyl-4-yl) ethyl]-1,3-oxazolidine-2,4-dione, obtained in step 3.2., and 2.5 ml (5.07 mmol) of methylamine (2M) in tetrahydrofuran, 0.250 g of pure product is obtained in the form of a white solid, following chromatography on silica gel, eluting with a 98/2 mixture of dichloromethane and methanol.
LC-MS: M+H=348
m.p. (° C.): 186-188° C.
$^1$H NMR (CDCl$_3$) δ (ppm): 2.80 (d, 3H); 2.95 (t, 2H); 3.55 (q, 2H); 4.60 (s, 2H); 4.90 (broad s, 1H); 6.15 (broad s, 1H); 7.33 (d, 2H); 7.40-7.70 (unresolved multiplet, 6H).

EXAMPLE 4

Compound 192

2-(methylamino)-2-oxoethyl 2-(3'-chloro-4'-fluoro-1,1'-biphenyl-4-yl)ethylcarbamate

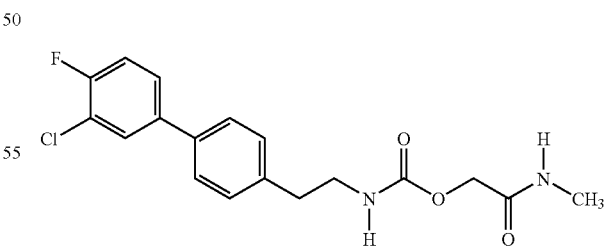

4.1. 2-(methylamino)-2-oxoethyl 2-(4-bromophenyl)ethylcarbamate

The procedure described in Example 2 (step 2.2.) is repeated. Starting from 2.6 g (9.15 mmol) of 3-[2-(4-bromophenyl)ethyl]-1,3-oxazolidine-2,4-dione, prepared in Example 3 (step 3.1.), and 18.3 ml (36.6 mmol) of methylamine (2M) in tetrahydrofuran, and after the product has been taken up in diisopropyl ether, 2.6 g of pure product are obtained in the form of a white solid.

m.p. (° C.): 122-124° C.

4.2. 2-(methylamino)-2-oxoethyl 2-(3'-chloro-4'-fluoro-1,1'-biphenyl-4-yl)ethylcarbamate The method described in Example 2 (step 2.2.) is used. Starting from 0.820 g (2.6 mmol) of 2-(methylamino)-2-oxoethyl 2-(4-bromophenyl)ethylcarbamate, obtained in step 4.1, and 0.4 g (2.86 mmol) of 3-chloro-4-fluorophenylboronic acid, 2.86 ml (5.72 mmol) of aqueous sodium carbonate solution (2M), 3 ml of ethanol and 0.15 g (0.13 mmol) of palladium tetrakis(triphenylphosphine), 0.42 g of pure product is obtained in the form of a white solid, following chromatography on silica gel, eluting with a 95/5 mixture of dichloromethane and methanol, followed by recrystallization from ethyl acetate.

LC-MS: M+H=365 m.p. (° C.): 178-180° C.

$^1$H NMR (CDCl$_3$) δ (ppm): 2.80 (d, 3H); 2.90 (t, 2H); 3.55 (q, 2H); 4.60 (s, 2H); 4.90 (broad s, 1H); 6.15 (broad s, 1H); 7.10-7.30 (unresolved multiplet, 3H); 7.40-7.55 (unresolved multiplet, 3H); 7.65 (dd, 1H).

EXAMPLE 5

Compound 9

2-(methylamino)-2-oxoethyl (3-chloro-4'-fluoro-1,1'-biphenyl-4-yl)methylcarbamate

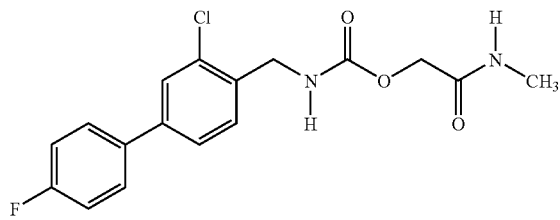

5.1. 3-chloro-4'-fluoro-1,1'-biphenyl-4-carboxylic acid

Under an inert atmosphere, 5 g (21.2 mmol) of 4-bromo-2-chlorobenzoic acid, 2.96 g (23.3 mmol) of 4-fluorophenylboronic acid and 31.8 ml (63.6 mmol) of aqueous sodium carbonate solution (2M) in suspension in 40 ml of toluene are introduced. Subsequently 0.80 g (0.70 mmol) of palladium tetrakis(triphenylphosphine) is added. The reaction mixture is subsequently refluxed overnight.

The salts are separated by filtration over Celite and then the filtrate is concentrated under reduced pressure. The residue is taken up in ethyl acetate and aqueous hydrochloric acid (4N). The organic phase is separated and is washed with saturated aqueous sodium chloride solution and the filtrate is concentrated under reduced pressure. This gives 3.1 g of acid in the form of a beige solid which is used as it is in the following step.

5.2. (3-chloro-4'-fluoro-1,1'-biphenyl-4-yl)methanol

A solution of 3.1 g (12.4 mmol) of 3-chloro-4'-fluoro-1,1'-biphenyl-4-carboxylic acid, prepared in step 5.1., in 50 ml of tetrahydrofuran is admixed dropwise at ambient temperature with 9.3 ml (18.56 mmol) of a solution (2M) of borane-dimethyl sulphide complex in tetrahydrofuran. Stirring is continued at ambient temperature for 18 hours.

The mixture is concentrated under reduced pressure and the residue is taken up in ethyl acetate and 100 ml of 0.1 N aqueous hydrochloric acid. The aqueous phase is separated and then is extracted twice with ethyl acetate. The organic phases are combined and are washed in succession with saturated aqueous sodium hydrogencarbonate solution and then saturated aqueous sodium chloride solution. The organic phase is dried over sodium sulphate and the filtrate is concentrated under reduced pressure. The residue thus obtained is purified by chromatography on silica gel, eluting with a 20/80 mixture of ethyl acetate and cyclohexane.

This gives 1.9 g of pure product in the form of a white solid.

m.p. (° C.): 86-88° C.

5.3. 3-chloro-4-(chloromethyl)-4'-fluoro-1,1'-biphenyl

A solution of 1.9 g (8 mmol) of (3-chloro-4'-fluoro-1,1'-biphenyl-4-yl)methanol, prepared in step 5.2., in 20 ml of chloroform is admixed dropwise at ambient temperature with 2.3 ml (32 mmol) of thionyl chloride. The mixture is stirred at ambient temperature for 18 hours and the filtrate is concentrated to dryness under reduced pressure. The residue obtained is coevaporated with 50 ml of toluene.

This gives 2 g of chloride in the form of an oil, which is used as it is in the following step.

5.4. 3-[(3-chloro-4'-fluoro-1,1'-biphenyl-4-yl)methyl]-1,3-oxazolidine-2,4-dione A solution of 0.5 g (1.96 mmol) of 3-chloro-4-(chloromethyl)-4'-fluoro-1,1'-biphenyl, prepared in step 5.3., 0.240 g (2.35 mmol) of 1,3-oxazolidine-2,4-dione and 0.45 g (3.92 mmol) of 1,1,3,3-tetramethylguanidine in 10 ml of tetrahydrofuran is refluxed for 18 hours.

The mixture is allowed to return to ambient temperature and is concentrated under reduced pressure. The residue is taken up in dichloromethane and water and the aqueous phase is separated and extracted twice with dichloromethane. The combined organic phases are washed with saturated aqueous sodium chloride solution and dried over sodium sulphate. Following evaporation of the solvent the residue obtained is purified by chromatography on silica gel, eluting with a 20/80 mixture of ethyl acetate and cyclohexane.

This gives 0.33 g of pure product in the form of a white solid.

m.p. (° C.): 108-110° C.

5.5. 2-(methylamino)-2-oxoethyl (3-chloro-4'-fluoro-1,1'-biphenyl-4-yl)methylcarbamate The procedure described in Example 2 (step 2.2.) is repeated. Starting from 0.33 g (0.9 mmol) of 3-[(3-chloro-4'-fluoro-1,1'-biphenyl-4-yl)methyl]-1,3-oxazolidine-2,4-dione, obtained in step 5.4., and 1.35 ml (2.7 mmol) of a solution of methylamine (2M) in tetrahydrofuran, 0.21 g of pure product is obtained in the form of a white solid, following chromatography on silica gel, eluting with a 95/5 mixture of dichloromethane and methanol, followed by recrystallization from ethyl acetate.

LC-MS: M+H=351 m.p. (° C.): 170-172° C.

$^1$H NMR (CDCl$_3$) δ (ppm): 2.90 (d, 3H); 4.50 (d, 2H); 4.60 (s, 2H); 5.40 (broad s, 1H); 6.10 (broad s, 1H); 7.15 (t, 2H); 7.40-7.70 (unresolved multiplet, 5H).

EXAMPLE 6

Compound 141

2-(methylamino)-2-oxoethyl 2-(3,4'-difluoro-1,1'biphenyl-4-yl)ethylcarbamate

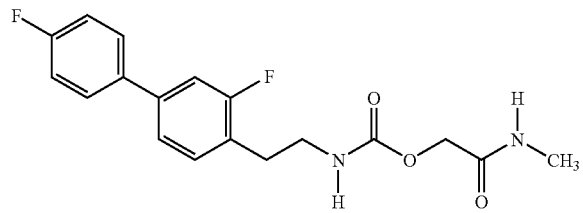

6.1. 3,4'-difluoro-1,1'-biphenyl-4-carboxaldehyde

The method described in Example 3 (step 3.2.) is used. Starting from 5.3 g (26 mmol) of 4-bromo-2-fluorobenzaldehyde, 4 g (28.6 mmol) of 4-fluorophenylboronic acid, 26 ml (52 mmol) of aqueous sodium carbonate (2M) solution and 0.9 g (0.78 mmol) of palladium tetrakis(triphenylphosphine), 3.4 g of pure product are obtained in the form of a white solid, following chromatography on silica gel, eluting with a 10/90 mixture of ethyl acetate and cyclohexane.

m.p. (° C.): 98° C.

6.2. 3,4'-difluoro-4-[(Z/E)-2-nitrovinyl]-1,1'-biphenyl

A suspension of 3.4 g (15.6 mmol) of 3,4'-difluoro-1,1'-biphenyl-4-carboxaldehyde, prepared in step 6.1., 1.5 ml (27.3 mmol) of nitromethane and 0.9 g (11.7 mmol) of ammonium acetate is heated at 50° C. overnight. It is allowed to return to ambient temperature and is taken up in dichloromethane and water. The aqueous phase is separated and extracted twice with dichloromethane and the combined organic phases are washed with saturated aqueous sodium chloride solution and dried over sodium sulphate. Following evaporation of the solvent, the residue obtained is purified by chromatography on silica gel, eluting with a 10/90 mixture of ethyl acetate and cyclohexane.

This gives 2 g of a pure product in the form of a yellow oil.

6.3. 2-(3,4'-difluoro-1,1'-biphenyl-4-yl)ethanamine

A suspension of 0.90 g (23.7 mmol) of lithium aluminum hydride in 20 ml of ether, cooled to approximately 0° C., is admixed dropwise with a solution of 2 g (7.7 mmol) of 3,4'-difluoro-4-(Z/E)-2-nitrovinyl]-1,1'-biphenyl, obtained in step 6.2., in 40 ml of a mixture of tetrahydrofuran and ether (1/1). The reaction mixture is subsequently heated at 60° C. for 2 hours.

It is allowed to return to ambient temperature and is filtered on paper and then the filtrate is treated with 0.9 ml of water and 0.9 ml of aqueous 15% sodium hydroxide solution and then 2.7 ml of water. It is stirred at ambient temperature for 1 hour. It is taken up in ethyl acetate, the aqueous phase is separated and extracted three times with ethyl acetate, the combined organic phases are washed with saturated aqueous sodium chloride solution and dried over sodium sulphate and the filtrate is concentrated under reduced pressure. The residue obtained is purified by chromatography on silica gel, eluting with a 97/3/0.3 mixture of dichloromethane, methanol and 28% aqueous ammonia.

This gives 0.31 g of product in the form of a colorless oil.

6.4. ethyl [(phenyloxycarbonyl)oxy]acetate

A solution of 25 g (240 mmol) of ethyl glycolate and 55 ml (315 mmol) of diisopropylethylamine in 500 ml of toluene is admixed slowly at ambient temperature with 32 ml (256 mmol) of phenyl chloroformate. Stirring is continued at ambient temperature for 2 hours.

The salt formed is separated off and the filtrate is concentrated under reduced pressure.

This gives 53.7 g of an oily product, which is used as it is in the following step.

6.5. ethyl (((2-(3,4'-difluoro-1,1'-biphenyl-4-yl)ethyl)amino)carbonyl)oxyacetate A solution of 0.31 g (1.33 mmol) of 2-(3,4'-difluoro-1,1'-biphenyl-4-yl)ethanamine, prepared in step 6.3., and 0.33 g (1.46 mmol) of ethyl [(phenyloxycarbonyl)oxy]acetate, obtained in step 6.4., in 10 ml of toluene is heated at 60° C. for 18 hours.

It is allowed to return to ambient temperature, the insoluble material is separated off by filtration and the filtrate is concentrated under reduced pressure. The residue is taken up in dichloromethane and the combined organic phases are washed with saturated aqueous sodium chloride solution and dried over sodium sulphate. Following evaporation of the solvent, the residue obtained is purified by chromatography on silica gel, eluting with a 30/70 mixture of ethyl acetate and cyclohexane.

This gives 0.33 g of pure product in the form of a white solid.

m.p. (° C.): 73-75° C.

6.6. 2-(methylamino)-2-oxoethyl 2-(3,4'-difluoro-1,1'-biphenyl-4-yl)ethylcarbamate The procedure of Example 2 (step 2.2.) is repeated. Starting from 0.33 g (0.9 mmol) of ethyl (((2-(3,4'-difluoro-1,1'-biphenyl-4-yl)ethyl)amino)carbonyl)oxyacetate prepared in step 6.5., and 1.35 ml (2.7 mmol) of a solution of methylamine (2M) in tetrahydrofuran, 0.210 g of pure product is obtained in the form of a white solid, following recrystallization from ethyl acetate.

LC-MS: M+H=349 m.p. (° C.): 164-166° C.

¹H NMR (CDCl₃) δ (ppm): 2.90 (d, 3H); 3.0 (t, 2H); 3.50 (q, 2H); 4.60 (s, 2H); 5.0 (broad s, 1H); 6.10 (broad s, 1H); 7.10-7.40 (unresolved multiplet, 5H); 7.55 (dd, 2H).

EXAMPLE 7

Compound 145

2-amino-2-oxoethyl 1-(4'-fluoro-1,1'-biphenyl-4-yl)cyclopropylmethylcarbamate

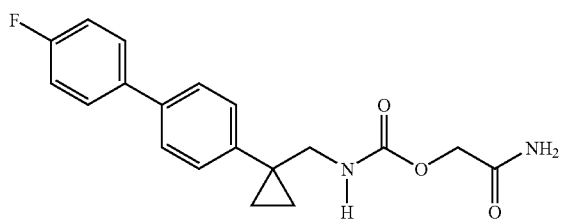

7.1. (4'-fluoro-1,1'-biphenyl-4-yl)acetonitrile

The method described in Example 3 (step 3.2.) is used. Starting from 4.12 g (32.48 mmol) of (4-bromophenyl)acetonitrile, 5 g (35.73 mmol) of 4-fluorophenylboronic acid, 32.48 ml (64.96 mmol) of aqueous sodium carbonate (2M) solution and 1.24 g (1.07 mmol) of palladium tetrakis(triphenylphosphine), 3.3 g of pure product are obtained in the form of a white solid, following chromatography on silica gel, eluting with a 15/85 mixture of ethyl acetate and cyclohexane.

m.p. (° C.): 100-102° C.

7.2. 1-(4'-fluoro-1,1'-biphenyl-4-yl)cyclopropanecarbonitrile

A suspension of 3.1 g (14.7 mmol) of (4'-fluoro-1,1'-biphenyl-4-yl)acetonitrile, prepared in step 7.1., 2.4 ml (29.4 mmol) of 1-bromo-2-chloroethane and 0.067 g (0.294 mmol) of N-triethylbenzylammonium chloride, heated to approximately 50° C., is admixed dropwise with 6.7 g (102.8 mmol) of aqueous 60% potassium hydroxide solution. Stirring is continued at 50° C. for 18 hours.

The mixture is allowed to return to ambient temperature, the insoluble material is separated off by filtration and the filtrate is taken up in ethyl acetate. The aqueous phase is separated and extracted three times with ethyl acetate. The combined organic phases are washed with saturated aqueous sodium chloride solution and dried over sodium sulphate. Following evaporation of the solvent, the residue obtained is purified by chromatography on silica gel, eluting with a 10/90 mixture of ethyl acetate and cyclohexane.

This gives 2.97 g of pure product in the form of a white solid.

m.p. (° C.): 70-72° C.

7.3. 1-[1-(4'-fluoro-1,1'-biphenyl-4-yl)cyclopropyl]methanamine

A solution of 2.5 g (10 mmol) of 1-(4'-fluoro-1,1'-biphenyl-4-yl)cyclopropylcarbonitrile, prepared in step 7.2., in 50 ml of tetrahydrofuran, cooled to approximately 0° C., is admixed dropwise with 10 ml (10 mmol) of a solution of lithium aluminum hydride (1M) in tetrahydrofuran. Stirring is continued at 0° C. for 1 hour and then at ambient temperature for 18 hours.

The mixture is filtered on paper and then the filtrate is treated with 0.4 ml of water and 0.4 ml of aqueous 15% sodium hydroxide solution and then 1.2 ml of water. The mixture is stirred at ambient temperature for 1 hour. It is taken up in ethyl acetate, the aqueous phase is separated and extracted twice with ethyl acetate, the combined organic phases are washed with saturated aqueous sodium chloride solution and dried over sodium sulphate and the filtrate is concentrated under reduced pressure.

This gives 2.1 g of product in the form of a white solid, which is used as it is in the following step.

m.p. (° C.): 100-102° C.

7.4. ethyl 1-((((((4'-fluoro-1,1'-biphenyl-4-yl)cyclopropyl)methyl)amino)carbonyl)oxy)acetate The procedure described in Example 6 (step 6.4.) is used. Starting from 2.4 g (10 mmol) of 1-[1-(4'-fluoro-1,1'-biphenyl-4-yl)cyclopropyl]methanamine, prepared in step 7.3., and 2.7 g (12 mmol) of ethyl [(phenyloxycarbonyl)oxy]acetate prepared in Example 6 (step 6.2.), 2.7 g of pure product are obtained in the form of a white solid, following chromatography on silica gel, eluting with a 15/85 mixture of ethyl acetate and cyclohexane.

m.p. (° C.): 96° C.

7.5. 2-amino-2-oxoethyl 1-(4'-fluoro-1,1'-biphenyl-4-yl)cyclopropylmethylcarbamate A solution of 1.4 g (3.77 mmol) of ethyl 1-((((((4'-fluoro-1,1'-biphenyl-4-yl)cyclopropyl)methyl)amino)carbonyl)oxy)acetate, obtained in step 7.4., in 10 ml of a 1/1 mixture of methanol and tetrahydrofuran is admixed with 11 ml (75 mmol) of a solution of ammonia (7N) in methanol. Stirring is continued at ambient temperatures for 12 hours.

Following concentration under reduced pressure, the residue obtained is purified by chromatography on silica gel, eluting with a 97/3 mixture of dichloromethane and methanol, followed by recrystallization from ethyl acetate.

This gives 0.738 g of pure product in the form of a white solid.

LC-MS: M+H=343
m.p. (° C.): 139-141° C.
¹H NMR (CDCl₃) δ (ppm): 1.0 (s, 4H); 3.50 (d, 2H); 4.55 (s, 2H); 4.90 (broad s, 1H); 5.50 (broad s, 1H); 5.90 (broad s, 1H); 7.15 (t, 2H); 7.30-7.70 (unresolved multiplet, 6H).

EXAMPLE 8

Compound 197

2-(methylamino)-2-oxoethyl 2-(3-phenyloxyphenyl)ethylcarbamate

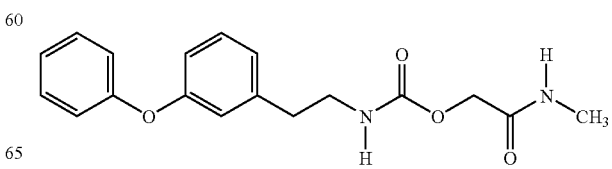

8.1. 2-(3-phenyloxyphenyl)ethanamine 1.38 g (6.59 mmol) of 3-phenoxyphenylacetonitrile and 1.57 g (6.59 mmol) of cobalt(II) chloride hexahydrate are dissolved in 25 ml of methanol. The solution is cooled with an iced water bath and 1.74 g (46 mmol) of sodium borohydride are added in portions. The reaction mixture is stirred overnight at ambient temperature. It is filtered on paper and rinsed with twice 25 ml of methanol. The filtrate is concentrated under reduced pressure and the residue is taken up in 50 ml of aqueous hydrochloric acid (1N) and 25 ml of ether. After distinct phases have separated out they are separated. The aqueous phase is washed with three times 25 ml of ether. The aqueous phase is rendered alkaline with 10 ml of aqueous 36% sodium hydroxide and extracted with three times 50 ml of dichloromethane. The extracts are washed with saturated aqueous sodium chloride solution and dried over sodium sulphate and the filtrate is concentrated under reduced pressure. This gives 0.67 g of product in the form of a brown-orange oil, which is used as it is in the following step.

8.2. Ethyl (((2-(3-phenyloxyphenyl)ethylamino)carbonyl)oxy)acetate

A mixture of 0.66 g (3.09 mmol) of 2-(3-phenyloxyphenyl)ethanamine, obtained in step 8.1, and 0.96 g (4.28 mmol) of ethyl [(phenyloxycarbonyl)oxy]acetate described in Example 6 in step 6.4., in 15 ml of toluene is heated at 60° C. overnight. The filtrate is concentrated under reduced pressure and the residue is purified by chromatography on silica gel, eluting with an 85/15 then 70/30 mixture of cyclohexane and ethyl acetate.

This gives 0.80 g of product in the form of an oil, which is used as it is in the following step.

8.3. 2-(methylamino)-2-oxoethyl 2-(3-phenyloxyphenyl)ethylcarbamate 0.70 g (2.30 mmol) of ethyl (((2-(3-phenyloxyphenyl)ethylamino)carbonyl)oxy)acetate, obtained in step 8.2., is dissolved in a mixture of 4.5 ml of a solution (2M) of methylamine in tetrahydrofuran and 4.5 ml of methanol. The solution is left overnight at ambient temperature. The filtrate is concentrated under reduced pressure and the residue is purified by chromatography on silica gel, eluting with a 98/2 then 96/4 mixture of dichloromethane and methanol. The product is subsequently recrystallized from a mixture of ethyl acetate and diisopropyl ether. This gives 0.51 g of fine white crystals.

LC-MS: M+H=329
m.p. (° C.): 82-84° C.
$^1$H NMR (DMSO-$d_6$) δ (ppm): 7.4-7.25 (m, 4H), 7.15 (t, 1H), 7.05-6.9 (m, 3H), 6.85 (s, 1H), 6.1 (m, 1H), 4.9 (m, 1H), 4.6 (s, 2H), 3.5 (q, 2H), 2.9-2.85 (m, 5H).

EXAMPLE 9

Compound 81

2-(methylamino)-2-oxoethyl 4-pyridin-2-ylbenzylcarbamate

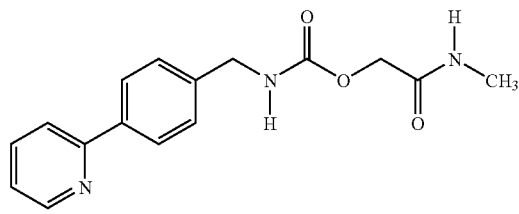

9.1. 3-(4-bromobenzyl)-1,3-oxazolidine-2,4-dione

A solution of 1.50 g (6 mmol) of 4-bromobenzyl bromide and 0.73 g (7.2 mmol) of 1,3-oxazolidine-2,4-dione in 6 ml of tetrahydrofuran is admixed dropwise with a solution of 1.39 g (12 mmol) of 1,1,3,3-tetramethylguanidine in 6 ml of tetrahydrofuran. The mixture is stirred at ambient temperature overnight. 50 ml of ice-cold aqueous hydrochloric acid (1N) and 100 ml of ethyl acetate are added. The organic phase is separated after settling out and washed successively with 25 ml of water and 25 ml of saturated aqueous sodium chloride solution. It is dried over sodium sulphate and the filtrate is concentrated under reduced pressure. The residue is purified by chromatography on silica gel, eluting with an 80/20 mixture of cyclohexane and ethyl acetate. 1.14 g of product are obtained in the form of white crystals.

m.p. (° C.): 88-90° C.

9.2. 3-(4-pyridin-2-ylbenzyl-1,3-oxazolidine-2,4-dione

Under an argon atmosphere, a mixture of 0.59 g (2.18 mmol) of 3-(4-bromobenzyl)-1,3-oxazolidine-2,4-dione, obtained in step 9.1., 1.60 g (4.35 mmol) of pyridin-2-yltri-n-butylstannane, 0.28 g (6.6 mmol) of lithium chloride and 0.125 g (0.10 mmol) of palladium tetrakis(triphenylphosphine) in 15 ml of toluene is heated at reflux overnight. It is cooled to ambient temperature, filtered on paper and rinsed in succession with 10 ml of toluene, 10 ml of ethyl acetate and 10 ml of toluene. The filtrates are concentrated under reduced pressure. The residue is taken up in 50 ml of acetonitrile and washed with four times 25 ml of n-hexane. The acetonitrile phase is concentrated under reduced pressure and the residue is purified by chromatography on silica gel, eluting with a 70/30 then 60/40 mixture of cyclohexane and ethyl acetate.

This gives 0.428 g of product in the form of a white powder.
m.p. (° C.): 166° C.

9.3. 2-(methylamino)-2-oxoethyl 4-pyridin-2-ylbenzylcarbamate 0.42 g (1.56 mmol) of 3-(4-pyridin-2-ylbenzyl)-1,3-oxazolidine-2,4-dione, obtained in step 9.2., is dissolved in a mixture of 3.5 ml of a solution (2M) of methylamine in tetrahydrofuran and 3.5 ml of methanol. The solution is left overnight at ambient temperature. 1.5 g of silica are added and the mixture is concentrated to dryness under reduced pressure, then purified by chromatography on silica gel, eluting with a 94/6 then 93/7 mixture of dichloromethane and methanol. The product is recrystallized from a mixture of isopropanol and diisopropyl ether.

This gives 0.30 g of product in the form of white flakes.
LC-MS: M+H=300
m.p. (° C.): 151-153° C.
$^1$H NMR (DMSO-$d_6$) δ (ppm): 8.6 (d, 1H), 8.05 (d, 2H), 7.95-7.7 (m, 4H, including 2 exchangeable in $D_2O$), 7.35 (d, 2H), 7.3 (m, 1H), 4.35 (s, 2H), 4.25 (d, 2H, s on exchange in $D_2O$), 2.6 (d, 3H, s on exchange in $D_2O$).

EXAMPLE 10

Compound 98

2-amino-2-oxoethyl 4-isoquinolin-4-ylbenzylcarbamate

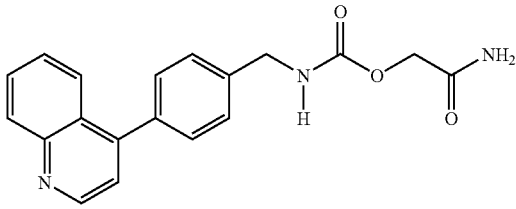

10.1. (4-isoquinolin-4-ylphenyl)methanol

Under an argon atmosphere, a mixture of 1.09 g (7.2 mmol) of (4-hydroxymethyl)phenylboronic acid, 1.24 g (6 mmol) of 4-bromoisoquinoline and 0.28 g (0.24 mmol) of palladium tetrakis(triphenylphosphine) in 50 ml of toluene and 10 ml of aqueous sodium carbonate solution (2M) is heated at reflux overnight. The filtrate is concentrated under reduced pressure and the residue is taken up in 150 ml of ethyl acetate and 40 ml of water. After the phases have settled and been separated, the organic phase is washed in succession with 20 ml of water and 20 ml of saturated aqueous sodium chloride solution. It is dried over sodium sulphate and the filtrate is concentrated under reduced pressure. The residue is purified by chromatography on silica gel, eluting with a 60/40 then 40/60 mixture of cyclohexane and ethyl acetate. This gives 1.12 g of a white solid.

m.p. (° C.): 130° C.

10.2. 3-(4-isoquinolin-4-ylbenzyl)-1,3-oxazolidine-2,4-dione 1.10 g (4.67 mmol) of (4-isoquinolin-4-ylphenyl)methanol, obtained in step 10.1., are dissolved in 10 ml of chloroform and 1.4 ml (19 mmol) of thionyl chloride are added dropwise. The mixture is stirred at ambient temperature overnight and the filtrate is concentrated to dryness under reduced pressure. The residue is coevaporated with two times 10 ml of dichloroethane. The residue is taken up in 15 ml of tetrahydrofuran. 0.56 g (5.54 mmol) of 1,3-oxazolidine-2,4-dione are added, followed dropwise by a solution of 1.60 g (13.9 mmol) of 1,1,3,3-tetramethylguanidine in 5 ml of tetrahydrofuran. The mixture is heated at reflux overnight. It is cooled to ambient temperature. 20 ml of iced water and 100 ml of ethyl acetate are added. After they have settled, the phases are separated. The organic phase is washed with three times 10 ml of water and 20 ml of saturated aqueous sodium chloride solution. It is dried over sodium sulphate and the filtrate is concentrated under reduced pressure. The residue is purified by chromatography on silica gel, eluting with a 50/50 then 40/60 mixture of cyclohexane and ethyl acetate. This gives 0.84 g of product in the form of a solid yellow foam.

m.p. (° C.): 65° C.

10.3. 2-amino-2-oxoethyl 4-isoquinolin-4-ylbenzylcarbamate 0.34 g (1.06 mmol) of 3-(4-isoquinolin-4-ylbenzyl)-1,3-oxazolidine-2,4-dione, obtained in step 10.2., is dissolved in a mixture of 6 ml of a solution (7N) of ammonia in methanol and 6 ml of tetrahydrofuran. The solution is left at ambient temperature overnight. 10 ml of dichloromethane and 1 g of silica are added and the mixture is concentrated to dryness under reduced pressure, then purified by chromatography on silica gel, eluting with a 95/5 then 92/8 mixture of dichloromethane and methanol. The product is recrystallized from a mixture of isopropanol and diisopropyl ether.

0.26 g of product is obtained in the form of a white cotton like substance.

LC-MS: M+H=336 m.p. (° C.): 181-183° C.

$^1$H NMR (DMSO-$d_6$) δ (ppm): 9.3 (s, 1H), 8.4 (s, 1H), 8.2 (d, 1H), 7.9-7 (m, 4H, including 1 exchangeable in $D_2O$), 7.5 (s, 4H), 7.3 (s, 1H, exchangeable in $D_2O$), 7.2 (s, 1H), 4.4 (s, 2H), 4.35 (d, 2H, s on exchange in $D_2O$).

EXAMPLE 11

Compound 171

2-(methylamino)-2-oxoethyl 2-(3'-cyano-1,1'-biphenyl-4-yl)ethylcarbamate

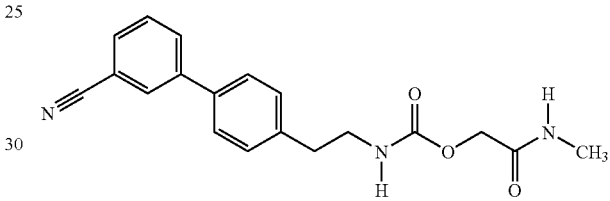

11.1. 4'-(2-hydroxyethyl)-3-biphenylcarbonitrile

A mixture of 3 g (14.92 mmol) of 2-(4-bromophenyl)ethanol, 2.85 g (19.40 mmol) of 3-cyanophenylboronic acid, 5.15 g (37.30 mmol) of potassium carbonate, 4.81 g (14.92 mmol) of tetran-butylammonium bromide and 0.067 g (0.30 mmol) of palladium diacetate in 15 ml of water is heated at 100° C. under an argon atmosphere overnight. It is cooled to ambient temperature, diluted with water and extracted with ethyl acetate. The organic phase is dried over sodium sulphate and evaporated. It is subsequently purified by chromatography on silica gel, eluting with a 70/30 then 50/50 mixture of cyclohexane and ethyl acetate, to give 2.90 g of product in the form of an oil, which is used as it is in the following step.

11.2. 4'-[2-(2,4-dioxo-1,3-oxazolidin-3-yl)ethyl]-3-biphenylcarbonitrile

A solution of 2.90 g (12.99 mmol) of 4'-(2-hydroxyethyl)-3-biphenylcarbonitrile, prepared in step 11.1., 2.7 ml (14.29 mmol) of triethylamine and 0.15 g (1.30 mmol) of 4-dimethylaminopyridine in 30 ml of dichloromethane, cooled with an ice bath, is admixed with 1.1 ml (14.29 mmol) of methanesulphonyl chloride. The mixture is subsequently stirred at ambient temperature for 2 hours. 100 ml of dichloromethane and 30 ml of saturated aqueous sodium chloride solution are added. The organic phase is separated off after settling, dried over sodium sulphate and evaporated to dryness to give 3.5 g of product in the form of an oil. The product is redissolved in 60 ml of tetrahydrofuran, and 1.40 g (13.94 mmol) of 1,3-oxazolidine-2,4-dione and 2.87 ml (23.23 mmol) of 1,1,3,3-tetramethylguanidine are added. The mixture is heated at 70° C. overnight. It is evaporated to dryness. The residue is taken up in a mixture of ethyl acetate and saturated aqueous sodium chloride solution. The organic phase is separated off after settling, dried over sodium sulphate and evaporated to dryness. The residue is purified by chromatography on silica gel, eluting with a 60/40 then 50/50 mixture of cyclohexane and ethyl acetate, to give 3.3 g of product in the form of a white solid.

Melting point (° C.): 121-123

11.3. 2-(methylamino)-2-oxoethyl 2-(3'-cyano-1,1'-biphenyl-4-yl)ethylcarbamate 2.0 g (6.53 mmol) of 4'-[2-(2,4-dioxo-1,3-oxazolidin-3-yl)ethyl]-3-biphenylcarbonitrile, prepared in step 11.2., are dissolved in a mixture of 13 ml of methanol and 9.8 ml of a 2N solution of methylamine (19.6 mmol) in tetrahydrofuran. The solution is left to react overnight and then evaporated to dryness and the residue is purified by chromatography on silica gel, eluting with a 96/4 then 95/5 mixture of dichloromethane and methanol. The product is recrystallized from a mixture of ethyl acetate and diisopropyl ether to give 1.07 g of product in the form of a white powder.

Melting point (° C.): 157-159
LC-MS: M+H=338
$^1$H NMR (CDCl$_3$) δ (ppm): 7.85 (s, 1H), 7.80 (dt, 1H), 7.65-7.50 (m, 4H), 7.35 (d, 2H), 6.05 (broad s, 1H), 4.95 (broad s, 1H), 4.60 (s, 2H), 3.55 (m, 2H), 2.95 (t, 2H), 2.85 (d, 3H).

EXAMPLE 12

Compound 84

2-amino-2-oxoethyl [4-(4-phenyl-1H-imidazol-1-yl)phenyl]methylcarbamate

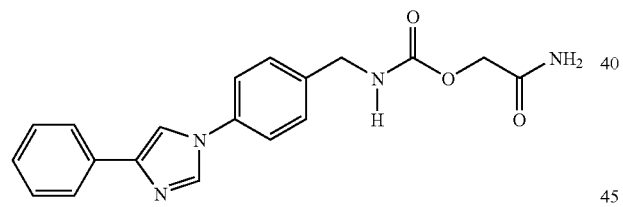

12.1. [4-(4-phenyl-1H-imidazol-1-yl)phenyl]methanol 3.04 g (20 mmol) of 4-(hydroxymethyl)phenylboronic acid, 1.44 g (10 mmol) of 4-phenylimidazole, 2.8 ml (20 mmol) of triethylamine and 1.64 ml (20 mmol) of pyridine are dissolved in 20 ml of dimethylformamide. 2.72 g (15 mmol) of copper diacetate are added and the mixture is stirred for 24 hours at ambient temperature. It is diluted with 200 ml of dichloromethane and 200 ml of aqueous 28% ammonia solution. After the phases have settled and been separated, the aqueous phase is extracted with 100 ml of dichloromethane. The organic phases are washed with 50 ml of saturated aqueous sodium chloride solution, dried over sodium sulphate and evaporated to dryness. The product is purified by chromatography on silica gel, eluting with a 97/3 then 95/5 mixture of dichloromethane and methanol. The product is recrystallized from a mixture of toluene and diisopropyl ether, to give 1.82 g of product in the form of white crystals.

Melting point (° C.): 137-139

12.2. 2-amino-2-oxoethyl [4-(4-phenyl-1H-imidazol-1-yl)phenyl]methylcarbamate A solution of 1.0 g (4 mmol) of [4-(4-phenyl-1H-imidazol-1-yl)phenyl]methanol, prepared in step 12.1., 0.485 g (4.80 mmol) of 1,3-oxazolidine-2,4-dione and 1.15 g (4.38 mmol) of triphenylphosphine in 16 ml of tetrahydrofuran, cooled by a bath of acetone and ice, is admixed dropwise with 0.80 g (4 mmol) of diisopropyl azodicarboxylate in solution in 2 ml of tetrahydrofuran. The mixture is subsequently warmed to ambient temperature again and stirred overnight. 9 ml of the solution are taken, to which are added 12 ml of a 7N ammonia solution (84 mmol) in methanol. The mixture is left to react overnight, admixed with 4 g of silica and evaporated to dryness. The product is purified by chromatography on silica gel, eluting with a 95/5 then 93/7 and 90/10 mixture of dichloromethane and methanol. The product is recrystallized from a mixture of methanol and diisopropyl ether, to give 0.429 g of product in the form of white crystals.

melting point (° C.): 200-203
LC-MS: M+H=351
$^1$H NMR (DMSO) δ (ppm): 8.30 (s, 1H), 8.20 (s, 1H), 7.80 (d+m, 3H), 7.65 (d, 2H), 7.45-7.20 (m, 7H), 4.35 (s, 2H), 4.25 (d, 2H).

EXAMPLE 13

Compound 224

2-amino-2-oxoethyl 2-[4-1H-pyrrolo[2,3-b]pyridin-1-yl)phenyl]ethylcarbamate

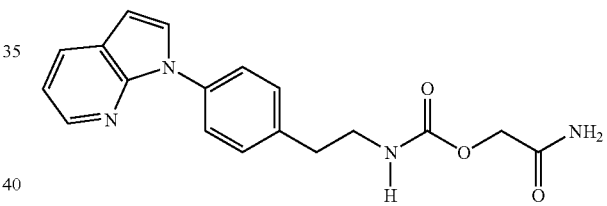

13.1. 2-[4-(1H-pyrrolo[2,3-b]pyridin-1-yl)phenyl]ethanol

A mixture of 1.24 g (5 mmol) of 2-(4-iodophenyl)ethanol, 0.62 g (5.25 mmol) of 7-azaindole, 2.33 g (11.0 mmol) of potassium phosphate, 0.082 g (1.0 mmol) of N,N'-dimethylethylenediamine and 0.095 g (0.50 mmol) of cuprous iodide in 4 ml of toluene is heated at 80° C. overnight with thorough stirring under an argon atmosphere. The mixture is cooled to ambient temperature and diluted with 150 ml of ethyl acetate and 50 ml of water. After the phases have settled and been separated, the organic phase is washed with 25 ml of water and 25 ml of saturated aqueous sodium chloride solution. It is dried over sodium sulphate and evaporated to dryness. The residue is purified by chromatography on silica gel, eluting with a 70/30 then 60/40 and 50/50 mixture of cyclohexane and ethyl acetate, to give 1.05 g of product in the form of an oil.

13.2. 3-{2-[4-(1H-pyrrolo[2,3-b]pyridin-1-yl)phenyl]ethyl}-1,3-oxazolidine-2,4-dione A solution of 1.0 g (4.20 mmol) of 2-[4-(1H-pyrrolo[2,3-b]pyridin-1-yl)phenyl]ethanol, prepared in step 13.1., 0.51 g (5.04 mmol) of 1,3-oxazolidine-2,4-dione and 1.21 g (4.62 mmol) of triphenylphosphine in 16 ml of tetrahydrofuran, cooled by a bath of acetone and ice, is admixed dropwise with 0.84 g (4.2 mmol) of diisopropyl azodicarboxylate in solution in 2 ml of tetrahydrofuran. The mixture is subsequently heated to ambient temperature again and stirred overnight. 4 g of silica are added and the mixture is evaporated to dryness. The residue is purified by chromatography on silica gel, eluting with a 70/30 then 60/40 then 50/50 and 40/60 mixture of cyclohexane and ethyl acetate, to give 1.52 g of product in the form of a sticky solid, which is used as it is in the following step.

13.3. 2-amino-2-oxoethyl 2-[4-1H-pyrrolo[2,3-b]pyridin-1-yl)phenyl]ethylcarbamate 0.80 g (2.49 mmol) of 3-{2-[4-(1H-pyrrolo[2,3-b]pyridin-1-yl)phenyl]ethyl]-1,3-oxazolidine-2,4-dione, prepared in step 13.2., is dissolved in 6 ml of tetrahydrofuran, and 12 ml of a 7N solution of ammonia (84 mmol) in methanol are added. The mixture is left to react overnight at ambient temperature. 2.5 g of silica are added and the mixture is evaporated to dryness. The residue is purified by chromatography on silica gel, eluting with a 98/2 then 96/4 and 94/6 mixture of dichloromethane and methanol. The product is recrystallized from a mixture of ethyl acetate and diisopropyl ether, to give 0.478 g of product in the form of white flakes.

Melting point (° C.): 110-112
LC-MS: M+H=339
$^1$H NMR (DMSO) δ (ppm): 8.30 (dd, 1H), 8.05 (d, 1H), 7.90 (d, 1H), 7.80 (d, 2H), 7.30 (d+m, 3H), 7.25-7.10 (m, 3H), 6.70 (d, 1H), 4.30 (s, 2H), 3.25 (broad t, 2H), 2.80 (t, 2H)

EXAMPLE 14

Compound 196

2-(methylamino)-2-oxoethyl 2-{4-[(4-chlorophenyl)oxy]phenyl}ethylcarbamate

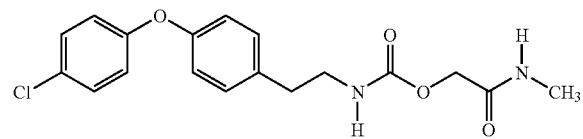

14.1. 2-(4-[(4-chlorophenyl)oxy]phenyl)ethanol

A mixture of 1.14 g (4.60 mmol) of 2-(4-iodophenyl)ethanol, 0.88 g (6.89 mmol) of 4-chlorophenol, 2.99 g (9.20 mmol) of cesium carbonate, 0.14 g (1.38 mmol) of N,N-dimethylglycine and 0.087 g (0.46 mmol) of cuprous iodide in 4 ml of dioxane is heated at 90° C. for 24 hours with thorough stirring under an argon atmosphere. It is cooled to ambient temperature and taken up in 150 ml of ethyl acetate and 50 ml of water. After the phases have settled and been separated, the organic phase is washed with 25 ml of water and 25 ml of saturated aqueous sodium chloride solution, dried over magnesium sulphate and evaporated to dryness. The residue is purified by chromatography on silica gel, eluting with an 85/15 then 75/25 mixture of cyclohexane and ethyl acetate, to give 0.68 g of product in the form of an oil.

14.2. 3-(2-(4-[(4-chlorophenyl)oxy]phenyl)ethyl)-1,3-oxazolidine-2,4-dione

A solution of 1.0 g (4.02 mmol) of 2-(4-[(4-chlorophenyl)oxy]phenyl)ethanol, prepared in accordance with Example 14.1., and 1.1 ml (7.89 mmol) of triethylamine in 12 ml of dichloromethane, cooled by an ice bath, is admixed with a solution of 0.60 g (5.24 mmol) of methanesulphonyl chloride in 2 ml of dichloromethane. The combined solutions are subsequently stirred at ambient temperature for 2 hours. They are diluted with 25 ml of water and 75 ml of dichloromethane. After the phases have settled and been separated, the organic phase is washed with 25 ml of water then 25 ml of saturated aqueous sodium chloride solution, dried over sodium sulphate and evaporated to dryness, to give 1.32 g of product in the form of an oil.

The product is redissolved in 12 ml of tetrahydrofuran. 0.50 g (5 mmol) of 1,3-oxazolidine-2,4-dione and a solution of 0.92 g (8.0 mmol) of 1,1,3,3-tetramethylguanidine in solution in 4 ml of tetrahydrofuran are added. The mixture is subsequently heated at reflux overnight. It is cooled with an ice bath and 25 ml of an aqueous 0.1N solution of hydrochloric acid and 100 ml of ethyl acetate are added. After the phases have settled, the organic phase is separated off and washed with two times 25 ml of water then with 25 ml of saturated aqueous sodium chloride solution, dried over sodium sulphate and evaporated to dryness. The residue is purified by chromatography on silica gel, eluting with an 85/15 then 75/25 and 65/35 mixture of cyclohexane and ethyl acetate, to give 1.20 g of product in the form of a white solid.

Melting point (° C.): 105-107

14.3. 2-(methylamino)-2-oxoethyl 2-{4-[(4-chlorophenyl)oxy]phenyl}ethylcarbamate 0.46 g (1.39 mmol) of 3-(2-(4-[(4-chlorophenyl)oxy]phenyl)ethyl)-1,3-oxazolidine-2,4-dione, prepared in step 14.2., is redissolved in a mixture of 3 ml of tetrahydrofuran and 6 ml of methanol. 3 ml of a 2M solution of methylamine (6 mmol) in tetrahydrofuran are added. The mixture is left to react at ambient temperature overnight and then 2 g of silica are added and the mixture is evaporated to dryness. The residue is purified by chromatography on silica gel, eluting with a 98/2 then 96/4 and 94/6 mixture of dichloromethane and methanol. The product is recrystallized from a mixture of ethyl acetate and diisopropyl ether, to give 0.40 g of product in the form of a white powder.

Melting point (° C.): 133-135
LC-MS: M+H=363
$^1$H NMR (DMSO) δ (ppm): 7.70 (m, 1H), 7.40 (d, 2H), 7.25 (d+m, 3H), 6.95 (m, 4H), 4.30 (s, 2H), 3.25 (m, 2H), 2.70 (t, 2H), 2.55 (d, 3H)

Table 1 which follows illustrates the chemical structures and physical properties of some compounds according to the invention. In this table:

all the compounds are in the free base form;
i-propyl, n-butyl and t-butyl represent isopropyl, linear butyl and tertiary butyl groups, respectively.

TABLE 1

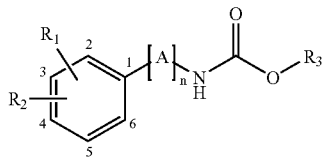

(I)

| No. | $[A]_n$ | $R_1$ | $R_2$ | $R_3$ | m.p. (° C.) |
|---|---|---|---|---|---|
| 1. | $CH_2$ | H | 4-phenyl | $CH_2CONHCH_3$ | 189-190 |
| 2. | $CH_2$ | H | 3-phenyl | $CH_2CONHCH_3$ | 128-129 |
| 3. | $CH_2$ | H | 4-phenyl | $CH_2CONH_2$ | 222-223 |
| 4. | $CH_2$ | H | 4-(2-F-phenyl) | $CH_2CONH_2$ | 176-177 |
| 5. | $CH_2$ | H | 3-(2-F-phenyl) | $CH_2CONH_2$ | 113-114 |
| 6. | $CH_2$ | H | 4-(3-F-phenyl) | $CH_2CONH_2$ | 201-202 |
| 7. | $CH_2$ | H | 3-(3-F-phenyl) | $CH_2CONH_2$ | 89-90 |
| 8. | $CH_2$ | H | 4-(4-F-phenyl) | $CH_2CONH_2$ | 226-227 |
| 9. | $CH_2$ | 2-Cl | 4-(4-F-phenyl) | $CH_2CONHCH_3$ | 170-172 |
| 10. | $CH(CH_3)$ | H | 4-(4-F-phenyl) | $CH_2CONH_2$ | 179-181 |
| 11. | $CH_2$ | H | 3-(4-F-phenyl) | $CH_2CONH_2$ | 100-101 |
| 12. | $CH_2$ | H | 4-(2-Cl-phenyl) | $CH_2CONH_2$ | 148-149 |
| 13. | $CH_2$ | H | 4-(3-Cl-phenyl) | $CH_2CONH_2$ | 187-188 |
| 14. | $CH_2$ | H | 4-(4-Cl-phenyl) | $CH_2CONH_2$ | 216-218 |
| 15. | $CH_2$ | H | 4-(2-$CF_3$-phenyl) | $CH_2CONH_2$ | 178-179 |
| 16. | $CH_2$ | H | 4-(3-$CF_3$-phenyl) | $CH_2CONH_2$ | 153-154 |
| 17. | $CH_2$ | H | 4-(4-$CF_3$-phenyl) | $CH_2CONH_2$ | 213-215 |
| 18. | $CH_2$ | H | 4-(2-$CF_3O$-phenyl) | $CH_2CONH_2$ | 177-179 |
| 19. | $CH_2$ | H | 4-(3-$CF_3O$-phenyl) | $CH_2CONH_2$ | 167-168 |
| 20. | $CH_2$ | H | 4-(4-$CF_3O$-phenyl) | $CH_2CONH_2$ | 218-220 |
| 21. | $CH_2$ | H | 4-(4-CN-phenyl) | $CH_2CONH_2$ | 221-222 |
| 22. | $CH_2$ | H | 4-(3-CN-phenyl) | $CH_2CONH_2$ | 126-127 |
| 23. | $CH_2$ | H | 4-(2-$CH_3CO$-phenyl) | $CH_2CONH_2$ | 184-185 |
| 24. | $CH_2$ | H | 4-(3-$CH_3CO$-phenyl) | $CH_2CONH_2$ | 142-145 |
| 25. | $CH_2$ | H | 4-(4-$CH_3CO$-phenyl) | $CH_2CONH_2$ | 231-233 |
| 26. | $CH_2$ | H | 4-(4-$CH_3SO_2$-phenyl) | $CH_2CONH_2$ | 233-235 |
| 27. | $CH_2$ | H | 4-(4-$CH_3CONH$-phenyl) | $CH_2CONH_2$ | 342* |
| 28. | $CH_2$ | H | 4-(3-$CH_3CONH$-phenyl) | $CH_2CONH_2$ | 189-190 |
| 29. | $CH_2$ | H | 3-(3-$CH_3CONH$-phenyl) | $CH_2CONH_2$ | 144-145 |
| 30. | $CH_2$ | H | 4-(3-$CH_3$-phenyl) | $CH_2CONH_2$ | 184-185 |
| 31. | $CH_2$ | H | 4-(4-$CH_3$-phenyl) | $CH_2CONH_2$ | 229-231 |
| 32. | $CH_2$ | H | 4-(4-$C_2H_5$-phenyl) | $CH_2CONH_2$ | 239-240 |
| 33. | $CH_2$ | H | 4-(3-i-propyl-phenyl) | $CH_2CONH_2$ | 154-155 |
| 34. | $CH_2$ | H | 4-(4-i-propyl-phenyl) | $CH_2CONH_2$ | 223-224 |
| 35. | $CH_2$ | H | 4-(4-t-butyl-phenyl) | $CH_2CONH_2$ | 189-190 |
| 36. | $CH_2$ | H | 4-(4-n-butyl-phenyl) | $CH_2CONH_2$ | 222-223 |
| 37. | $CH_2$ | H | 4-(3-phenyl-phenyl) | $CH_2CONH_2$ | 182-183 |
| 38. | $CH_2$ | H | 4-(2-$CH_3O$-phenyl) | $CH_2CONH_2$ | 153-154 |
| 39. | $CH_2$ | H | 4-(2-$CH_3S$-phenyl) | $CH_2CONH_2$ | 128-129 |
| 40. | $CH_2$ | H | 3-(2-$CH_3O$-phenyl) | $CH_2CONH_2$ | 148-149 |
| 41. | $CH_2$ | H | 4-(3-$CH_3O$-phenyl) | $CH_2CONH_2$ | 140-141 |
| 42. | $CH_2$ | H | 3-(3-$CH_3O$-phenyl) | $CH_2CONH_2$ | 315* |
| 43. | $CH_2$ | H | 4-(4-$CH_3O$-phenyl) | $CH_2CONH_2$ | 229-230 |
| 44. | $CH_2$ | H | 3-(4-$CH_3O$-phenyl) | $CH_2CONH_2$ | 134-135 |
| 45. | $CH_2$ | H | 4-(3-$C_2H_5O$-phenyl) | $CH_2CONH_2$ | 234-236 |
| 46. | $CH_2$ | H | 4-(4-$C_2H_5O$-phenyl) | $CH_2CONH_2$ | 233-234 |
| 47. | $CH_2$ | H | 4-(3-benzyloxy-phenyl) | $CH_2CONH_2$ | 175-176 |
| 48. | $CH_2$ | H | 4-(4-benzyloxy-phenyl) | $CH_2CONH_2$ | 229-231 |
| 49. | $CH_2$ | H | 4-(2-F,5-F-phenyl) | $CH_2CONH_2$ | 180-182 |
| 50. | $CH_2$ | H | 4-(3-F,4-F-phenyl) | $CH_2CONH_2$ | 236-237 |
| 51. | $CH_2$ | H | 4-(3-F,5-F-phenyl) | $CH_2CONH_2$ | 174-176 |
| 52. | $CH_2$ | H | 4-(2-Cl,3-Cl-phenyl) | $CH_2CONH_2$ | 170-171 |
| 53. | $CH_2$ | H | 4-(2-Cl,4-Cl-phenyl) | $CH_2CONH_2$ | 116-117 |
| 54. | $CH_2$ | H | 4-(2-Cl,5-Cl-phenyl) | $CH_2CONH_2$ | 119-122 |
| 55. | $CH_2$ | H | 4-(3-Cl,4-Cl-phenyl) | $CH_2CONH_2$ | 173-176 |
| 56. | $CH_2$ | H | 4-(3-Cl,5-Cl-phenyl) | $CH_2CONH_2$ | 161-162 |
| 57. | $CH_2$ | H | 4-(2-F,3-$CH_3O$-phenyl) | $CH_2CONH_2$ | 114-115 |
| 58. | $CH_2$ | H | 4-(3-F,4-$CH_3O$-phenyl) | $CH_2CONH_2$ | 225-226 |
| 59. | $CH_2$ | H | 4-(4-F,3-$CH_3$-phenyl) | $CH_2CONH_2$ | 201-202 |
| 60. | $CH_2$ | H | 4-(4-F,3-Cl-phenyl) | $CH_2CONH_2$ | 158-159 |
| 61. | $CH_2$ | H | 4-(2,4-$(CH_3O)_2$-phenyl) | $CH_2CONH_2$ | 166-167 |
| 62. | $CH_2$ | H | 4-(2,5-$(CH_3O)_2$-phenyl) | $CH_2CONH_2$ | 132-133 |
| 63. | $CH_2$ | H | 4-(3,4-$OCH_2O$-phenyl) | $CH_2CONH_2$ | 329* |
| 64. | $CH_2$ | H | 4-(3,4-$(CH_3)_2$-phenyl) | $CH_2CONH_2$ | 190-191 |
| 65. | $CH_2$ | H | 4-(3-$CF_3$,5-$CF_3$-phenyl) | $CH_2CONH_2$ | 176-177 |
| 66. | $CH_2$ | H | 4-(5-Cl,2-$CH_3O$-phenyl) | $CH_2CONH_2$ | 145-146 |
| 67. | $CH_2$ | H | 4-phenyloxy | $CH_2CONH_2$ | 166-168 |

TABLE 1-continued

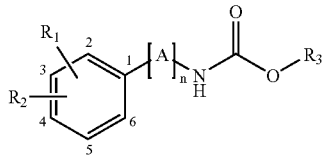

(I)

| No. | [A]$_n$ | R$_1$ | R$_2$ | R$_3$ | m.p. (° C.) |
|---|---|---|---|---|---|
| 68. | CH$_2$ | H | 4-phenyloxy | CH$_2$CONHCH$_3$ | 128-130 |
| 69. | CH$_2$ | H | 4-(4-Cl-phenyloxy) | CH$_2$CONH$_2$ | 184-186 |
| 70. | CH$_2$ | H | 4-(4-Cl-phenyloxy) | CH$_2$CONHCH$_3$ | 159-161 |
| 71. | CH$_2$ | H | 3-phenyloxy | CH$_2$CONH$_2$ | 106-107 |
| 72. | CH$_2$ | H | 3-phenyloxy | CH$_2$CONHCH$_3$ | 100-102 |
| 73. | CH$_2$ | H | 3-(4-Cl-phenyloxy) | CH$_2$CONH$_2$ | 110-112 |
| 74. | CH$_2$ | H | 3-(4-Cl-phenyloxy) | CH$_2$CONHCH$_3$ | 85-87 |
| 75. | CH$_2$ | H | 4-benzoyl | CH$_2$CONH$_2$ | 161-163 |
| 76. | CH$_2$ | H | 4-benzoyl | CH$_2$CONHCH$_3$ | 149-151 |
| 77. | CH$_2$ | H | 3-benzoyl | CH$_2$CONHCH$_3$ | 91-93 |
| 78. | CH$_2$ | H | 4-phenylsulphonyl | CH$_2$CONH$_2$ | 88-90 |
| 79. | CH$_2$ | H | 4-phenylsulphonyl | CH$_2$CONHCH$_3$ | 363* |
| 80. | CH$_2$ | H | 4-(pyridin-3-yl) | CH$_2$CONH$_2$ | 160-162 |
| 81. | CH$_2$ | H | 4-(pyridin-2-yl) | CH$_2$CONHCH$_3$ | 151-153 |
| 82. | CH$_2$ | H | 4-(pyrazin-2-yl) | CH$_2$CONHCH$_3$ | 186-189 |
| 83. | CH$_2$ | H | 4-(thien-3-yl) | CH$_2$CONH$_2$ | 311-312 |
| 84. | CH$_2$ | H | 4-phenylimidazol-1-yl | CH$_2$CONH$_2$ | 200-203 |
| 85. | CH$_2$ | H | 4-phenylimidazol-1-yl | CH$_2$CONHCH$_3$ | 191-193 |
| 86. | CH$_2$ | H | 3-phenylimidazol-1-yl | CH$_2$CONH$_2$ | 170-172 |
| 87. | CH$_2$ | H | 4-(4-CH$_3$-thien-2-yl) | CH$_2$CONH$_2$ | 203-204 |
| 88. | CH$_2$ | H | 4-(benzo[b]thien-3-yl) | CH$_2$CONH$_2$ | 144-145 |
| 89. | CH$_2$ | H | 4-(3,5-(CH$_3$)$_2$-isoxazol-4-yl) | CH$_2$CONH$_2$ | 164-165 |
| 90. | CH$_2$ | H | 4-(1,2,3-thiadiazol-4-yl) | CH$_2$CONHCH$_3$ | 185-187 |
| 91. | CH$_2$ | H | 4-(dibenzo[b,d]furan-2-yl) | CH$_2$CONH$_2$ | 194-195 |
| 92. | CH$_2$ | H | 4-(2-phenyl-ethylen-1-yl) | CH$_2$CONH$_2$ | 236-238 |
| 93. | CH$_2$ | H | 4-(naphth-1-yl) | CH$_2$CONH$_2$ | 154-156 |
| 94. | CH$_2$ | H | 4-(4-CH$_3$-(naphth-1-yl) | CH$_2$CONH$_2$ | 114-115 |
| 95. | CH$_2$ | H | 4-(naphth-2-yl) | CH$_2$CONH$_2$ | 240-241 |
| 96. | CH$_2$ | H | 4-(quinolin-8-yl) | CH$_2$CONH$_2$ | 140-142 |
| 97. | CH$_2$ | H | 4-(isoquinolin-1-yl) | CH$_2$CONH$_2$ | 180-183 |
| 98. | CH$_2$ | H | 4-(isoquinolin-4-yl) | CH$_2$CONH$_2$ | 181-183 |
| 99. | CH$_2$ | H | 4-(isoquinolin-4-yl) | CH$_2$CONHCH$_3$ | 187-189 |
| 100. | CH$_2$ | H | 4-(benzimidazol-1-yl) | CH$_2$CONH$_2$ | 208-211 |
| 101. | CH$_2$ | H | 4-(pyrrolo[2,3-b]pyridinyl) | CH$_2$CONH$_2$ | 113-116 |
| 102. | CH$_2$ | H | 3-(pyrrolo[2,3-b]pyridinyl) | CH$_2$CONH$_2$ | 130-132 |
| 103. | CH$_2$CH$_2$ | H | H | CH$_2$CONH$_2$ | 130-131 |
| 104. | (CH$_2$)$_3$ | H | H | CH$_2$CONH$_2$ | 113-114 |
| 105. | (CH$_2$)$_3$ | H | 4-phenyl | CH$_2$CONH$_2$ | 187-189 |
| 106. | (CH$_2$)$_3$ | H | 3-phenyl | CH$_2$CONH$_2$ | 151-153 |
| 107. | (CH$_2$)$_4$ | H | H | CH$_2$CONH$_2$ | 251* |
| 108. | (CH$_2$)$_4$ | H | 4-phenyl | CH$_2$CONH$_2$ | 171-173 |
| 109. | (CH$_2$)$_4$ | H | 3-phenyl | CH$_2$CONH$_2$ | 127-129 |
| 110. | (CH$_2$)$_5$ | H | H | CH$_2$CONHCH$_3$ | 86-88 |
| 111. | (CH$_2$)$_5$ | H | 4-phenyl | CH$_2$CONH$_2$ | 225-227 |
| 112. | (CH$_2$)$_5$ | H | 3-phenyl | CH$_2$CONH$_2$ | 135-137 |
| 113. | (CH$_2$)$_6$ | H | H | CH$_2$CONH$_2$ | 109-111 |
| 114. | (CH$_2$)$_6$ | H | H | CH$_2$CONHCH$_3$ | 70-72 |
| 115. | (CH$_2$)$_7$ | H | H | CH$_2$CONHCH$_3$ | 83-85 |
| 116. | 4-cyclohexyl(CH$_2$)$_2$ | H | H | CH$_2$CONH$_2$ | 141-142 |
| 117. | CH$_2$CH$_2$ | H | 2-Cl | CH$_2$CONH$_2$ | 80-90 |
| 118. | CH$_2$CH$_2$ | H | 3-Cl | CH$_2$CONH$_2$ | 79-80 |
| 119. | CH$_2$CH$_2$ | H | 4-Cl | CH$_2$CONH$_2$ | 124-125 |
| 120. | CH$_2$CH$_2$ | 2-Cl | 4-Cl | CH$_2$CONH$_2$ | 104-105 |
| 121. | CH$_2$CH$_2$ | H | 4-F | CH$_2$CONH$_2$ | 132-133 |
| 122. | CH$_2$CH$_2$ | H | 4-CH$_3$ | CH$_2$CONH$_2$ | 159-160 |
| 123. | CH$_2$CH$_2$ | H | 4-Br | CH$_2$CONH$_2$ | 162-163 |
| 124. | CH$_2$CH$_2$ | H | 3-CF$_3$ | CH$_2$CONHCH$_3$ | 96-98 |
| 125. | CH$_2$CH$_2$ | H | 4-CF$_3$ | CH$_2$CONHCH$_3$ | 140-142 |
| 126. | CH$_2$CH$_2$ | H | 4-CF$_3$O | CH$_2$CONHCH$_3$ | 126-127 |
| 127. | CH$_2$CH$_2$ | H | 4-OH | CH$_2$CONHCH$_3$ | 98-99 |
| 128. | CH$_2$CH$_2$ | H | 4-CH$_3$O | CH$_2$CONH$_2$ | 133-134 |
| 129. | CH$_2$CH$_2$ | H | 4-CH$_3$O | CH$_2$CONHCH$_3$ | 101-102 |
| 130. | CH$_2$CH$_2$ | H | 4-CH$_3$O | CH$_2$CONHCH$_2$CH$_3$ | 95-96 |
| 131. | CH$_2$CH$_2$ | H | 3-CH$_3$O | CH$_2$CONH$_2$ | 86-87 |
| 132. | CH$_2$CH$_2$ | 4-CH$_3$O | 3-CH$_3$O | CH$_2$CONH$_2$ | 110-111 |
| 133. | CH$_2$CH$_2$ | 5-CH$_3$O | 2-CH$_3$O | CH$_2$CONH$_2$ | 140-141 |
| 134. | CH$_2$CH$_2$ | H | 2-CH$_3$O | CH$_2$CONH$_2$ | 100-101 |

TABLE 1-continued

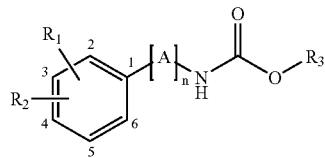
(I)

| No. | [A]$_n$ | R$_1$ | R$_2$ | R$_3$ | m.p. (° C.) |
|---|---|---|---|---|---|
| 135. | CH$_2$CH$_2$ | H | 4-phenyl | CH$_2$CONH$_2$ | 187-188 |
| 136. | CH$_2$CH$_2$ | H | 4-phenyl | CH$_2$CONHCH$_3$ | 158-159 |
| 137. | CH$_2$CH$_2$ | H | 4-phenyl | CH$_2$CONHCH$_2$CH$_3$ | 152-153 |
| 138. | CH$_2$CH$_2$ | H | 4-(2-F-phenyl) | CH$_2$CONHCH$_3$ | 106-107 |
| 139. | CH$_2$CH$_2$ | H | 4-(3-F-phenyl) | CH$_2$CONHCH$_3$ | 157-158 |
| 140. | CH$_2$CH$_2$ | H | 4-(4-F-phenyl) | CH$_2$CONHCH$_3$ | 182-184 |
| 141. | CH$_2$CH$_2$ | 2-F | 4-(4-F-phenyl) | CH$_2$CONHCH$_3$ | 164-166 |
| 142. | CH$_2$CH$_2$ | 2-Cl | 4-(4-F-phenyl) | CH$_2$CONHCH$_3$ | 141-143 |
| 143. | C(CH$_3$)$_2$CH$_2$ | H | 4-(4-F-phenyl) | CH$_2$CONH$_2$ | 134-136 |
| 144. | C(CH$_3$)$_2$CH$_2$ | H | 4-(4-F-phenyl) | CH$_2$CONHCH$_3$ | 112-114 |
| 145. | C[CH$_2$CH$_2$]CH$_2$ | H | 4-(4-F-phenyl) | CH$_2$CONH$_2$ | 139-141 |
| 146. | C[CH$_2$CH$_2$]CH$_2$ | H | 4-(4-F-phenyl) | CH$_2$CONHCH$_3$ | 152-154 |
| 147. | CH$_2$CH$_2$ | H | 4-(2-Cl-phenyl) | CH$_2$CONHCH$_3$ | 148-149 |
| 148. | CH$_2$CH$_2$ | H | 4-(3-Cl-phenyl) | CH$_2$CONHCH$_3$ | 181-182 |
| 149. | CH$_2$CH$_2$ | H | 4-(4-Cl-phenyl) | CH$_2$CONH$_2$ | 198-200 |
| 150. | CH$_2$CH$_2$ | H | 4-(4-Cl-phenyl) | CH$_2$CONHCH$_3$ | 186-188 |
| 151. | CH$_2$CH$_2$ | H | 4-(2-CH$_3$-phenyl) | CH$_2$CONHCH$_3$ | 108-109 |
| 152. | CH$_2$CH$_2$ | H | 4-(3-CH$_3$-phenyl) | CH$_2$CONHCH$_3$ | 126-127 |
| 153. | CH$_2$CH$_2$ | H | 4-(4-CH$_3$-phenyl) | CH$_2$CONHCH$_3$ | 171-172 |
| 154. | CH$_2$CH$_2$ | H | 4-(4-CH$_3$CH$_2$-phenyl) | CH$_2$CONHCH$_3$ | 166-167 |
| 155. | CH$_2$CH$_2$ | H | 4-(3-i-propyl-phenyl) | CH$_2$CONHCH$_3$ | 355* |
| 156. | CH$_2$CH$_2$ | H | 4-(3-i-propyl-phenyl) | CH$_2$CONHCH$_2$CH$_3$ | 103-104 |
| 157. | CH$_2$CH$_2$ | H | 4-(4-n-butyl-phenyl) | CH$_2$CONHCH$_3$ | 168-169 |
| 158. | CH$_2$CH$_2$ | H | 4-(4-t-butyl-phenyl) | CH$_2$CONHCH$_3$ | 174-175 |
| 159. | CH$_2$CH$_2$ | H | 4-(2-CH$_3$S-phenyl) | CH$_2$CONHCH$_3$ | 359* |
| 160. | CH$_2$CH$_2$ | H | 4-(2-CH$_3$O-phenyl) | CH$_2$CONHCH$_3$ | 111-112 |
| 161. | CH$_2$CH$_2$ | H | 4-(3-CH$_3$O-phenyl) | CH$_2$CONHCH$_3$ | 343* |
| 162. | CH$_2$CH$_2$ | H | 4-(4-CH$_3$O-phenyl) | CH$_2$CONHCH$_3$ | 182-183 |
| 163. | CH$_2$CH$_2$ | H | 4-(3-CH$_3$CH$_2$O-phenyl) | CH$_2$CONHCH$_3$ | 105-106 |
| 164. | CH$_2$CH$_2$ | H | 4-(2-phenyloxy-phenyl) | CH$_2$CONHCH$_3$ | 405* |
| 165. | CH$_2$CH$_2$ | H | 4-(2-benzyloxy-phenyl) | CH$_2$CONHCH$_3$ | 112-113 |
| 166. | CH$_2$CH$_2$ | H | 4-(4-CF$_3$O-phenyl) | CH$_2$CONHCH$_3$ | 170-171 |
| 167. | CH$_2$CH$_2$ | H | 4-(3-CF$_3$-phenyl) | CH$_2$CONHCH$_3$ | 131-132 |
| 168. | CH$_2$CH$_2$ | H | 4-(4-CF$_3$-phenyl) | CH$_2$CONHCH$_3$ | 198-199 |
| 169. | CH$_2$CH$_2$ | H | 4-(4-CN-phenyl) | CH$_2$CONH$_2$ | 196-198 |
| 170. | CH$_2$CH$_2$ | H | 4-(3-CN-phenyl) | CH$_2$CONH$_2$ | 184-186 |
| 171. | CH$_2$CH$_2$ | H | 4-(3-CN-phenyl) | CH$_2$CONHCH$_3$ | 157-159 |
| 172. | CH$_2$CH$_2$ | H | 4-(3-CH$_3$CO-phenyl) | CH$_2$CONHCH$_3$ | 102-103 |
| 173. | CH$_2$CH$_2$ | H | 4-(4-CH$_3$O$_2$C-phenyl) | CH$_2$CONHCH$_3$ | 184-185 |
| 174. | CH$_2$CH$_2$ | H | 4-(3-NO$_2$-phenyl) | CH$_2$CONHCH$_3$ | 163-164 |
| 175. | CH$_2$CH$_2$ | H | 4-(4-(CH$_3$)$_2$N-phenyl) | CH$_2$CONHCH$_3$ | 170-171 |
| 176. | CH$_2$CH$_2$ | H | 4-(2-Cl,3-Cl-phenyl) | CH$_2$CONHCH$_3$ | 149-150 |
| 177. | CH$_2$CH$_2$ | H | 4-(2-Cl,4-Cl-phenyl) | CH$_2$CONH$_2$ | 132-134 |
| 178. | CH$_2$CH$_2$ | H | 4-(2-Cl,4-Cl-phenyl) | CH$_2$CONHCH$_3$ | 147-149 |
| 179. | CH$_2$CH$_2$ | H | 4-(2-Cl,4-Cl-phenyl) | CH$_2$CONHCH$_2$CH$_3$ | 164-166 |
| 180. | CH$_2$CH$_2$ | H | 4-(3-Cl,4-Cl-phenyl) | CH$_2$CONHCH$_3$ | 163-164 |
| 181. | CH$_2$CH$_2$ | H | 4-(2-CH$_3$O,4-CH$_3$O-phenyl) | CH$_2$CONHCH$_3$ | 134-135 |
| 182. | CH$_2$CH$_2$ | H | 4-(2-CH$_3$O,5-CH$_3$O-phenyl) | CH$_2$CONHCH$_3$ | 373* |
| 183. | CH$_2$CH$_2$ | H | 4-(2-CH$_3$O,6-CH$_3$O$_2$-phenyl) | CH$_2$CONHCH$_3$ | 148-149 |
| 184. | CH$_2$CH$_2$ | H | 4-(3-CH$_3$O,4-CH$_3$O-phenyl) | CH$_2$CONH$_2$ | 108-109 |
| 185. | CH$_2$CH$_2$ | H | 4-(3-CH$_3$O,4-CH$_3$O-phenyl) | CH$_2$CONHCH$_3$ | 132-133 |
| 186. | CH$_2$CH$_2$ | H | 4-(3,4-(OCH$_2$O)- | CH$_2$CONHCH$_3$ | 165-166 |
| 187. | CH$_2$CH$_2$ | H | 4-(3-CH$_3$,4-CH$_3$-phenyl) | CH$_2$CONHCH$_3$ | 144-145 |
| 188. | CH$_2$CH$_2$ | H | 4-(3-CF$_3$,5-CF$_3$-phenyl) | CH$_2$CONHCH$_3$ | 136-137 |
| 189. | CH$_2$CH$_2$ | H | 4-(2-F,3-CH$_3$O-phenyl) | CH$_2$CONHCH$_3$ | 130-131 |
| 190. | CH$_2$CH$_2$ | H | 4-(5-Cl,2-CH$_3$O-phenyl) | CH$_2$CONHCH$_3$ | 106-107 |
| 191. | CH$_2$CH$_2$ | H | 4-(3-Cl,4-F-phenyl) | CH$_2$CONH$_2$ | 151-153 |
| 192. | CH$_2$CH$_2$ | H | 4-(3-Cl,4-F-phenyl) | CH$_2$CONHCH$_3$ | 178-180 |
| 193. | CH$_2$CH$_2$ | H | 4-(3-CH$_3$,4-F-phenyl) | CH$_2$CONHCH$_3$ | 155-156 |
| 194. | CH$_2$CH$_2$ | H | 4-phenyloxy | CH$_2$CONHCH$_3$ | 111-113 |
| 195. | CH$_2$CH$_2$ | H | 4-(4-Cl-phenyloxy) | CH$_2$CONH$_2$ | 156-158 |
| 196. | CH$_2$CH$_2$ | H | 4-(4-Cl-phenyloxy) | CH$_2$CONHCH$_3$ | 133-135 |
| 197. | CH$_2$CH$_2$ | H | 3-phenyloxy | CH$_2$CONHCH$_3$ | 82-84 |
| 198. | CH$_2$CH$_2$ | H | 4-(2-F-benzyloxy) | CH$_2$CONHCH$_3$ | 112-113 |
| 199. | CH$_2$CH$_2$ | H | 4-(3-F-benzyloxy) | CH$_2$CONHCH$_3$ | 127-128 |

TABLE 1-continued

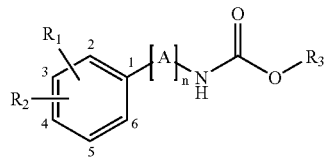

(I)

| No. | [A]$_n$ | R$_1$ | R$_2$ | R$_3$ | m.p. (° C.) |
|---|---|---|---|---|---|
| 200. | CH$_2$CH$_2$ | H | 4-(4-F-benzyloxy) | CH$_2$CONHCH$_3$ | 129-130 |
| 201. | CH$_2$CH$_2$ | H | 4-(2-CH$_3$-benzyloxy) | CH$_2$CONHCH$_3$ | 103-104 |
| 202. | CH$_2$CH$_2$ | H | 4-(3-CH$_3$-benzyloxy) | CH$_2$CONHCH$_3$ | 112-113 |
| 203. | CH$_2$CH$_2$ | H | 4-(4-CH$_3$-benzyloxy) | CH$_2$CONHCH$_3$ | 135-136 |
| 204. | CH$_2$CH$_2$ | H | 4-(2-CF$_3$-benzyloxy) | CH$_2$CONHCH$_3$ | 110-111 |
| 205. | CH$_2$CH$_2$ | H | 4-(3-CF$_3$-benzyloxy) | CH$_2$CONHCH$_3$ | 103-104 |
| 206. | CH$_2$CH$_2$ | H | 4-(4-CF$_3$-benzyloxy) | CH$_2$CONHCH$_3$ | 127-128 |
| 207. | CH$_2$CH$_2$ | H | 4-(3-CH$_3$O-benzyloxy) | CH$_2$CONHCH$_3$ | 92-93 |
| 208. | CH$_2$CH$_2$ | H | 4-(4-CH$_3$O$_2$C-benzyloxy) | CH$_2$CONHCH$_3$ | 145-146 |
| 209. | CH$_2$CH$_2$ | H | 4-(3-phenylpropyl-1-oxy) | CH$_2$CONHCH$_3$ | 110-111 |
| 210. | CH$_2$CH$_2$ | H | 4-(pyridin-2-yl) | CH$_2$CONH$_2$ | 140-142 |
| 211. | CH$_2$CH$_2$ | H | 4-(pyridin-3-yl) | CH$_2$CONH$_2$ | 134-136 |
| 212. | CH$_2$CH$_2$ | H | 4-(pyridin-4-yl) | CH$_2$CONH$_2$ | 206-208 |
| 213. | CH$_2$CH$_2$ | H | 4-(pyrimidin-5-yl) | CH$_2$CONH$_2$ | 240-242 |
| 214. | CH$_2$CH$_2$ | H | 4-(furan-2-yl) | CH$_2$CONHCH$_3$ | 150-151 |
| 215. | CH$_2$CH$_2$ | H | 4-(thien-2-yl) | CH$_2$CONHCH$_3$ | 157-158 |
| 216. | CH$_2$CH$_2$ | H | 4-(thien-3-yl) | CH$_2$CONHCH$_3$ | 174-175 |
| 217. | CH$_2$CH$_2$ | H | 4-(benzo[b]thien-3-yl) | CH$_2$CONHCH$_3$ | 124-125 |
| 218. | CH$_2$CH$_2$ | H | 4-(2-CH$_3$O,4-CH$_3$O-pyrimidin-5-yl) | CH$_2$CONHCH$_3$ | 142-143 |
| 219. | CH$_2$CH$_2$ | H | 4-(quinolin-2-yl) | CH$_2$CONH$_2$ | 214-216 |
| 220. | CH$_2$CH$_2$ | H | 4-(quinolin-4-yl) | CH$_2$CONH$_2$ | 181-183 |
| 221. | CH$_2$CH$_2$ | H | 4-(quinolin-8-yl) | CH$_2$CONHCH$_3$ | 130-131 |
| 222. | CH$_2$CH$_2$ | H | 4-(isoquinolin-1-yl) | CH$_2$CONH$_2$ | 138-140 |
| 223. | CH$_2$CH$_2$ | H | 4-(isoquinolin-4-yl) | CH$_2$CONH$_2$ | 193-195 |
| 224. | CH$_2$CH$_2$ | H | 4-(pyrrolo[2,3-b]pyridinyl) | CH$_2$CONH$_2$ | 110-112 |
| 225. | CH$_2$CH$_2$ | H | 4-(pyrrolo[2,3-b]pyridinyl) | CH$_2$CONHCH$_3$ | 124-126 |

*M + H (LC-MS)

The compounds of the invention were subjected to pharmacological tests permitting determination of their inhibitory effect on the enzyme FAAH (Fatty Acid Amide Hydrolase).

The inhibitory activity was demonstrated in a radioenzymatic assay based on measuring the product of hydrolysis (ethanolamine [1-$^3$H]) of anandamide [ethanolamine 1-$^3$H] by FAAH (*Life Sciences* (1995), 56, 1999-2005 and *Journal of Pharmacology and Experimental Therapeutics* (1997), 283, 729-734). Accordingly, mouse brains (minus the cerebellum) are removed and stored at −80° C. Membrane homogenates are prepared at the time of use by homogenizing the tissues in a Polytron in a 10 mM Tris HCl buffer (pH 8.0) containing 150 mM NaCl and 1 mM EDTA. The enzyme reaction is subsequently conducted in 70 µl of buffer, containing bovine serum albumin without fatty acids (1 mg/ml). In succession, the test compounds, at various concentrations, anandamide [ethanolamine 1-$^3$H] (specific activity: 15-20 Ci/mmol) diluted to 10 µM with cold anandamide, and the membrane preparation (400 µg of frozen tissue per assay) are added. After 15 minutes at 25° C., the enzyme reaction is terminated by adding 140 µl of chloroform/methanol. (2:1). The mixture is stirred for 10 minutes then centrifuged for 15 minutes at 3500 g. An aliquot (30 µl) of the aqueous phase, containing the ethanolamine [1-$^3$H], is counted by liquid scintillation. Under these conditions, the most active compounds of the invention exhibit IC$_{50}$ values (concentration inhibiting by 50% the control enzyme activity of FAAH) of between 0.001 and 1 µm.

Table 2 below presents the IC$_{50}$ values of some compounds according to the invention.

TABLE 2

| Compound No. | IC$_{50}$ |
|---|---|
| 192 | 0.102 µM |
| 171 | 0.108 µM |
| 194 | 0.142 µM |
| 150 | 0.063 µM |
| 178 | 0.140 µM |

It is therefore apparent that the compounds according to the invention have an inhibitory effect on the FAAH enzyme.

The in vivo activity of the compounds of the invention was evaluated in an analgesia test. Accordingly, intraperitoneal (i.p.) administration of PBQ (phenylbenzoquinone, 2 mg/kg in a 0.9% sodium chloride solution containing 5% of ethanol) to male OF1 mice weighing 25 to 30 g causes abdominal stretches, on average 30 twists or contractions during the period from 5 to 15 minutes after injection. The test compounds are administered orally in suspension in Tween 80 at 0.5%, 60 minutes or 120 minutes before the administration of PBQ. Under these conditions, the most potent compounds of the invention reduce by 35 to 70% the number of stretches induced by PBQ, within a dose range of between 1 and 30 mg/kg.

Table 3 below presents the results of the analgesia test for some compounds according to the invention.

TABLE 3

| Compound No. | Reduction in number of stretches (%) |
|---|---|
| 192 | −43% (a) |
| 171 | −51% (a) |
| 194 | −55% (b) |
| 150 | −57% (b) |
| 178 | −53% (b) |

(a) 1 mg/kg p.o. at 2 hours;
(b) 3 mg/kg p.o. at 1 hour

The enzyme FAAH (*Chemistry and Physics of Lipids*, (2000), 108, 107-121) catalyses the hydrolysis of endogenous derivatives of amides and of esters of various fatty acids such as N-arachidonoylethanolamine (anandamide), N-palmitoylethanolamine, N-oleoylethanolamine, oleamide or 2-arachidonoylglycerol. These derivatives exert various pharmacological activities by interacting, inter alia, with cannabinoid and vanilloid receptors.

The compounds of the invention block this degradation pathway and increase the tissue level of these endogenous substances. They can be used in this respect in the prevention and treatment of pathologies in which endogenous cannabinoids and/or any other substrates metabolized by the FAAH enzyme are involved.

Mention may be made, for example, of the following diseases and conditions:

Pain, especially acute or chronic pain of the neurogenic type: migraine, neuropathic pain, including forms associated with the herpes virus and with diabetes;

acute or chronic pain associated with inflammatory diseases: arthritis, rheumatoid arthritis, osteoarthritis, spondylitis, gout, vasculitis, Crohn's disease, irritable bowel syndrome;

acute or chronic peripheral pain;

dizziness, vomiting, nausea, especially those subsequent to chemotherapy;

eating disorders, especially anorexia and cachexia of various kinds;

neurological and psychiatric pathologies: shaking, dyskinesia, dystonia, spasticity, obsessive-compulsive behavior, Tourette's syndrome, all forms of depression and anxiety of any kind and cause, mood disorders, psychoses;

acute and chronic neurodegenerative diseases:

Parkinson's disease, Alzheimer's disease, senile dementia, Huntington's chorea, lesions associated with cerebral ischaemia and with cranial and with medullary trauma;

epilepsy;

sleep disorders, including sleep apnea;

cardiovascular diseases, especially hypertension, cardiac arrhythmias, arteriosclerosis, heart attack, cardiac ischaemia;

renal ischaemia;

cancers: benign skin tumors, papillomas and brain tumors, prostate tumors, brain tumors (glioblastomas, medulloepitheliomas, medulloblastomas, neuroblastomas, tumors of embryonic origin, astrocytomas, astroblastomas, ependyomas, oligodendrogliomas, plexus tumor, neuroepitheliomas, epiphyseal tumor, ependymoblastomas, malignant meningiomas, sarcomatoses, malignant melanomas, schwannomas);

disorders of the immune system, especially autoimmune diseases; psoriasis, lupus erythematosis, diseases of the connective tissue or collagen diseases, Sjögren's syndrome, ankylosing spondylarthritis, undifferentiated spondylarthritis, Behcet's disease, haemolytic autoimmune anaemias, multiple sclerosis, amyotrophic lateral sclerosis, amyloses, transplant rejection, diseases affecting the plasmocytic line;

allergic diseases: immediate or delayed hypersensitivity, allergic rhinitis or conjunctivitis, contact dermatitis;

parasitic, viral or bacterial infectious diseases: AIDS, meningitis; inflammatory diseases, especially diseases of the joints: arthritis, rheumatoid arthritis, osteoarthritis, spondylitis, gout, vasculitis, Crohn's disease, irritable bowel syndrome, osteoporosis; ocular conditions; ocular hypertension, glaucoma;

pulmonary conditions: diseases of the respiratory tracts, bronchospasms, coughing, asthma, chronic bronchitis, chronic obstruction of the respiratory tracts, emphysema;

gastrointestinal diseases: irritable bowel syndrome, intestinal inflammatory disorders, ulcers, diarrhea; urinary incontinence and bladder inflammation.

The use of a compound of formula (I), in base, salt, hydrate or pharmaceutically acceptable solvate form, for preparing a medicinal product intended for treating the abovementioned pathologies forms an integral part of the invention.

The invention additionally relates to medicinal products which comprise a compound of formula (I), or a salt, or else a hydrate or a pharmaceutically acceptable solvate of the compound of formula (I). These medicinal products are employed in therapy, particularly in the treatment of the abovementioned pathologies.

In accordance with another of its aspects the present invention relates to pharmaceutical compositions comprising as active principle at least one compound according to the invention. These pharmaceutical compositions contain an effective dose of a compound according to the invention, or a salt, or a hydrate, or a pharmaceutically acceptable solvate of the said compound, and optionally one or more pharmaceutically acceptable excipients.

The said excipients are selected, in accordance with the pharmaceutical form and desired mode of administration, from the customary excipients, which are known to the person skilled in the art.

In the pharmaceutical compositions of the present invention for oral, sublingual, subcutaneous, intramuscular, intravenous, topical, local, intrathecal, intranasal, transdermal, pulmonary, ocular or rectal administration, the active principle of formula (I) above, or its salt, solvate or hydrate where appropriate, may be administered in single-dose administration form, as a mixture with conventional pharmaceutical excipients, to animals and to humans for the prophylaxis or treatment of the above disorders or diseases.

The unit-dose administration forms which are appropriate include oral forms such as tablets, soft or hard gelatin capsules, powders, granules, chewing gums and oral solutions or suspensions, forms for sublingual, buccal, intratracheal, intraocular and intranasal administration and for administration by inhalation, forms for subcutaneous, intramuscular or intravenous administration and forms for rectal or vaginal administration. For topical application the compounds according to the invention can be used in creams, ointments or lotions.

By way of example, a single-dose administration form of a compound according to the invention in tablet form may comprise the following components:

| | |
|---|---|
| Compound according to the invention | 50.0 mg |
| Mannitol | 223.75 mg |
| Sodium croscaramellose | 6.0 mg |

| | |
|---|---|
| Maize starch | 15.0 mg |
| Hydroxypropylmethylcellulose | 2.25 mg |
| Magnesium stearate | 3.0 mg |

The said single-dose forms contain a dose permitting daily administration of from 0.01 to 20 mg of active principle per kg of body weight, depending on the pharmaceutical form.

There may be particular cases in which higher or lower doses are appropriate; such doses also belong to the invention. In accordance with customary practice, the dose appropriate to each patient is determined by the doctor according to the method of administration, the weight and the response of the said patient.

According to another of its aspects, the invention also relates to a method of treating the pathologies indicated above, which comprises administering an effective dose of a compound according to the invention, one of its pharmaceutically acceptable salts, or a solvate or a hydrate of the said compound.

What is claimed is:

1. A compound of formula (I):

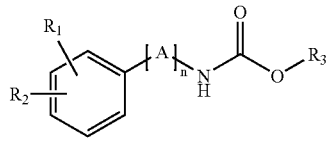

wherein:

n represents an integer from 1 to 7;

A is selected from the group consisting of X, Y and Z;

X represents a $C_{1-2}$-alkylene group optionally substituted by one or more $C_{1-12}$-alkyl, $C_{3-7}$-cycloalkyl or $C_{3-7}$-cycloalkyl-$C_{1-6}$-alkylene groups;

Y represents either a $C_2$-alkenylene group optionally substituted by one or more $C_{1-12}$-alkyl, $C_{3-7}$-cycloalkyl or $C_{3-7}$-cycloalkyl-$C_{1-6}$-alkylene groups; or a $C_2$-alkynylene group;

Z represents a $C_{3-7}$-cycloalkyl group of formula:

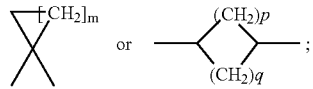

m represents an integer of from 1 to 5;

p and q represent integers and are defined such that p+q is a number of from about 1 to 5;

$R_1$ is selected from the group consisting of a hydrogen or halogen or a hydroxy, cyano, nitro, $C_{1-4}$-alkyl, $C_{1-4}$-alkoxy, $C_{1-4}$-thioalkyl, $C_{1-4}$-fluoroalkyl, $C_{1-4}$-fluoroalkoxy and a $C_{1-4}$-fluorothioalkyl group;

$R_2$ is selected from the group consisting of hydrogen, halogen, cyano, nitro, hydroxy, $C_{1-4}$-alkyl, $C_{1-4}$-alkoxy, $C_{1-4}$-thioalkyl, $C_{1-4}$-fluoroalkyl, $C_{1-4}$-fluoroalkoxy, $C_{1-4}$-fluorothioalkyl group, or a group selected from phenyl, naphthyl, biphenyl, phenylethylenyl, naphthylethylenyl, pyridinyl, pyrimidinyl, pyrazinyl, pyridazinyl, indanyl, indenyl, quinolinyl, isoquinolinyl, thienyl, furanyl, pyrrolyl, imidazolyl, pyrazolyl, oxazolyl, thiazolyl, isoxazolyl, isothiazolyl, thiadiazolyl, oxadiazolyl, phenylimidazolyl, benzothienyl, benzofuranyl, dibenzofuranyl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio-, phenylsulphonyl, benzoyl, benzyloxy, phenylethoxy, phenylpropoxy, naphthyloxy, naphthylmethoxy, naphthylethoxy, naphthylpropoxy, quinolinoxy and isoquinolinoxy and optionally substituted by one or more substituents selected from a halogen or a cyano, nitro, $C_{1-4}$-alkyl, hydroxy, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidinyl, pyrrolidinyl, morpholinyl, $NR_6R_7$, $NHCOR_6$, $COR_6$, $CO_2R_6$, $SO_2R_6$, —O—($C_{1-3}$-alkylene)-O— and 4-piperazinyl optionally substituted by a $C_{1-3}$-alkyl or by a benzyl;

$R_6$ and $R_7$ are selected from the group consisting of independently of one another a $C_{1-3}$-alkyl group or a phenyl; and $R_3$ represents a group of formula $CHR_4CONHR_5$ in which $R_4$ represents a hydrogen or a $C_{1-3}$-alkyl group and $R_5$ represents a hydrogen or a $C_{1-3}$-alkyl, $C_{3-5}$-cycloalkyl or $C_{3-7}$-cycloalkyl-$C_{1-6}$-alkylene group;

or a pharmaceutically acceptable salt thereof with the exception of 2-amino-2-oxoethyl benzylcarbamate.

2. The compound of formula (I) according to claim 1, wherein:

when n is 1:

A is selected from the group consisting of X, Y and Z;

X represents a $C_{1-2}$-alkylene group optionally substituted by one or more $C_{1-12}$-alkyl, $C_{3-7}$-cycloalkyl or $C_{3-7}$-cycloalkyl-$C_{1-6}$-alkylene groups;

Y represents either a $C_2$-alkenylene group optionally substituted by one or more $C_{1-12}$-alkyl, $C_{3-7}$-cycloalkyl or $C_{3-7}$-cycloalkyl-$C_{1-6}$-alkylene groups; or a $C_2$-alkynylene group;

Z represents a $C_{3-7}$-cycloalkyl group of formula:

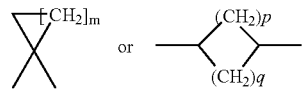

m represents an integer from 1 to 5;

p and q represent integers and are defined such that p+q is a number from 1 to 5;

$R_1$ is selected from the group consisting of a hydrogen or halogen or a hydroxy, cyano, nitro, $C_{1-4}$-alkyl, $C_{1-4}$-alkoxy, $C_{1-4}$-thioalkyl, $C_{1-4}$-fluoroalkyl, $C_{1-4}$-fluoroalkoxy and $C_{1-4}$-fluorothioalkyl group;

$R_2$ is selected from the group consisting of a halogen, cyano, nitro, hydroxy, $C_{1-4}$-alkyl, $C_{1-4}$-alkoxy, $C_{1-4}$-thioalkyl, $C_{1-4}$-fluoroalkyl, $C_{1-4}$-fluoroalkoxy, $C_{1-4}$-fluorothioalkyl group, or a group selected from phenyl, naphthyl, biphenyl, phenylethylenyl, naphthylethylenyl, pyridinyl, pyrimidinyl, pyrazinyl, pyridazinyl, indanyl, indenyl, quinolinyl, isoquinolinyl, thienyl, furanyl, pyrrolyl, imidazolyl, pyrazolyl, oxazolyl, thiazolyl, isoxazolyl, isothiazolyl, thiadiazolyl, oxadiazolyl, phenylimidazolyl, benzothienyl, benzofuranyl, dibenzofuranyl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsuiphonyl, benzoyl, benzyloxy, phenylethoxy, phenylpropoxy, naphthyloxy, naphthylmethoxy, naphthylethoxy, naphthylpropoxy, quinolinoxy and isoquinolinoxy and optionally substituted by one or more substituents selected from a halogen and a cyano, nitro, $C_{1-4}$-alkyl, hydroxy, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidinyl, pyrrolidinyl, morpholinyl, $NR_6R_7$, $NHCOR_6$, $COR_6$, $CO_2R_6$, $SO_2R_6$, —O—$(C_{1-3}$-alkylene$)$-O— and 4-piperazinyl optionally substituted by a $C_{1-3}$-alkyl or by a benzyl; $R_6$ and $R_7$ represent independently of one another a $C_{1-3}$-alkyl group or a phenyl;

and, $R_3$ represents a group of formula $CHR_4CONHR_5$ in which $R_4$ represents a hydrogen or a $C_{1-3}$-alkyl group and $R_5$ represents a hydrogen or a $C_{1-3}$-alkyl, $C_{3-5}$-cycloalkyl or $C_{3-7}$-cycloalkyl-$C_{1-6}$-alkylene group;

when n represents an integer from 2 to 7:

A is selected from the group consisting of X, Y and Z;

X represents a $C_{1-2}$-alkylene group optionally substituted by one or more $C_{1-12}$-alkyl, $C_{3-7}$-cycloalkyl or $C_{3-7}$-cycloalkyl-$C_{1-6}$-alkylene groups;

Y represents either a $C_2$-alkenylene group optionally substituted by one or more $C_{1-12}$-alkyl, $C_{3-7}$-cycloalkyl or $C_{3-7}$-cycloalkyl-$C_{1-6}$-alkylene groups; or a $C_2$-alkynylene group;

Z represents a $C_{3-7}$-cycloalkyl group of formula:

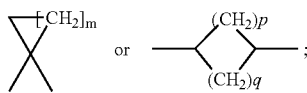

m represents an integer from 1 to 5;

p and q represent integers and are defined such that p+q is a number from 1 to 5;

$R_1$ is selected from the group consisting of hydrogen or halogen or a hydroxy, cyano, nitro, $C_{1-4}$-alkyl, $C_{1-4}$-alkoxy, $C_{1-4}$-thioalkyl, $C_{1-4}$-fluoroalkyl, $C_{1-4}$-fluoroalkoxy and a $C_{1-4}$-fluorothioalkyl group;

$R_2$ is selected from the group consisting of hydrogen, halogen, cyano, nitro, hydroxy, $C_{1-4}$-alkyl, $C_{1-4}$-alkoxy, $C_{1-4}$-thioalkyl, $C_{1-4}$-fluoroalkyl, $C_{1-4}$-fluoroalkoxy, $C_{1-4}$-fluorothioalkyl group, or a group selected from phenyl, naphthyl, biphenyl, phenylethylenyl, naphthylethylenyl, pyridinyl, pyrimidinyl, pyrazinyl, pyridazinyl, indanyl, indenyl, quinolinyl, isoquinolinyl thienyl, furanyl, pyrrolyl, imidazolyl, pyrazolyl, oxazolyl, thiazolyl, isoxazolyl, isothiazolyl, thiadiazolyl, oxadiazolyl, phenylimidazolyl, benzothienyl, benzofuranyl, dibenzofuranyl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsulphonyl, benzoyl, benzyloxy, phenylethoxy, phenylpropoxy, naphthyloxy, naphthylmethoxy, naphthylethoxy, naphthylpropoxy, quinolinoxy and isoquinolinoxy and optionally substituted by one or more substituents selected from a halogen and a cyano, nitro, $C_{1-4}$-alkyl, hydroxy, $C_{1-4}$-alkoxy, $C_{1-4}$-thioalkyl, $C_{1-3}$-fluoroalkyl, $C_{1-3}$-fluoroalkoxy, $C_{1-4}$-fluorothioalkyl, phenyloxy, benzyloxy, piperidinyl, pyrrolidinyl, morpholinyl, $NR_6R_7$, $NHCOR_6$, $COR_6$, $CO_2R_6$, $SO_2R_6$, —O—$(C_{1-3}$-alkylene$)$-O— and 4-piperazinyl optionally substituted by a $C_{1-3}$-alkyl or by a benzyl;

$R_6$ and $R_7$ are selected from the group consisting of a $C_{1-3}$-alkyl group and a phenyl;

and $R_3$ represents a group of formula $CHR_4CONHR_5$ in which $R_4$ represents a hydrogen or a $C_{1-3}$-alkyl group and $R_5$ represents a hydrogen or a $C_{1-3}$-alkyl, $C_{3-5}$-cycloalkyl or $C_{3-7}$-cycloalkyl-$C_{1-6}$-alkylene group; or a pharmaceutically acceptable salt thereof.

3. The compound of formula (I) according to claim 2, wherein:

n represents an integer from 1 to 5;

A is selected from the group consisting of X and Z;

X is a $C_{1-2}$-alkylene group optionally substituted by one or more $C_{1-3}$-alkyl groups;

Z represents a $C_{3-7}$-cycloalkyl group of formula:

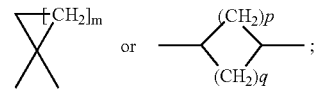

m represents an integer from 1 to 5;

p and q represent integers and are defined such that p+q is a number from 1 to 5;

$R_1$ is selected from the group consisting of hydrogen, halogen and $C_{1-4}$-alkoxy group;

$R_2$ is selected from the group consisting of hydrogen, halogen, hydroxy, $C_{1-4}$-alkyl, $C_{1-4}$-alkoxy, $C_{1-4}$-fluoroalkyl, $C_{1-4}$-fluoroalkoxy, phenyl, naphthyl, biphenyl, phenylethylenyl, pyridinyl, pyrimidinyl, pyrazinyl, quinolinyl, isoquinolinyl, thienyl, furanyl, isoxazolyl, thiadiazolyl, phenylimidazolyl, benzothienyl, dibenzofuranyl, benzimidazolyl, pyrrolopyridinyl, phenyloxy, phenylsulphonyl, benzoyl, benzyloxy and phenylpropoxy, optionally substituted by one or more substituents selected from halogen, cyano, nitro, $C_{1-4}$-alkyl, $C_{1-4}$-alkoxy, $C_{1-4}$-thioalkyl, $C_{1-3}$-fluoroalkyl, $C_{1-3}$-fluoroalkoxy, phenyloxy, or benzyloxy, $NR_6R_7$, $NHCOR_6$, $COR_6$, $CO_2R_6$, $SO_2R_6$ and —O—$(C_{1-3}$-alkylene$)$-O—, $R_6$ and $R_7$ represent independently of one another a $C_{1-3}$-alkyl group;

$R_3$ represents a group of formula $CHR_4CONHR_5$ in which $R_4$ represents a hydrogen or a $C_{1-3}$-alkyl group and $R_5$ represents a hydrogen or a $C_{1-3}$-alkyl group, $C_{3-5}$-cycloalkyl group or $C_{3-7}$-cycloalkyl-$C_{1-6}$-alkylene group;

or a pharmaceutically acceptable salt thereof.

4. The compound of formula (I) according to claim 3, wherein:

n represents an integer from 1 to 5;

A represents a $C_{1-2}$-alkylene group;

$R_1$ represents a hydrogen or a halogen;

$R_2$ is selected from the group consisting of phenyl, naphthyl, phenyloxy, benzyloxy, pyridinyl, quinolinyl, isoquinolinyl, phenylimidazolyl and pyrrolopyridinyl, optionally substituted by one or more substituents selected from halogen, a cyano, a $C_{1-4}$-alkyl group, $C_{1-4}$-alkoxy, $C_{1-3}$-fluoroalkyl, or $C_{1-3}$-fluoroalkoxy;

$R_3$ represents a group of formula $CHR_4CONHR_5$ in which $R_4$ represents a hydrogen and $R_5$ represents a hydrogen or a $C_{1-3}$-alkyl group, $C_{3-5}$-cycloalkyl group or $C_{3-7}$-cycloalkyl-$C_{1-6}$-alkylene group;

or a pharmaceutically acceptable salt thereof.

5. The compound of formula (I) according to claim 1, wherein:

n is 1;

A is X and X is methylene optionally substituted by one or more $C_{1-12}$-alkyl, $C_{3-7}$-cycloalkyl or $C_{3-7}$-cycloalkyl-$C_{1-6}$-alkylene groups;

$R_1$ represents a hydrogen, halogen, hydroxy, cyano, nitro, $C_{1-4}$-alkyl, $C_{1-4}$-alkoxy, $C_{1-4}$-thioalkyl, $C_{1-4}$-fluoroalkyl, $C_{1-4}$-fluoroalkoxy or $C_{1-4}$-fluorothioalkyl group;

$R_2$ is selected from the group consisting of a halogen, cyano, nitro, hydroxy, $C_{1-4}$-alkyl, $C_{1-4}$-alkoxy, $C_{1-4}$-thioalkyl, $C_{1-4}$-fluoroalkyl, $C_{1-4}$-fluoroalkoxy, $C_{1-4}$-fluorothioalkyl group, or a group selected from phenyl, naphthyl, biphenyl, phenylethylenyl, naphthylethylenyl, pyridinyl, pyrimidinyl, pyrazinyl, pyridazinyl, indanyl, indenyl, quinolinyl, isoquinolinyl thienyl, furanyl, pyrrolyl, imidazolyl, pyrazolyl, oxazolyl, thiazolyl, isoxazolyl, isothiazolyl, thiadiazolyl, oxadiazolyl phenylimidazolyl, benzothienyl, benzofuranyl, dibenzofuranyl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsulphonyl, benzoyl, benzyloxy, phenylethoxy, phenylpropoxy, naphthyloxy, naphthylmethoxy, naphthylethoxy, naphthylpropoxy, quinolinoxy and isoquinolinoxy and optionally substituted by one or more substituents selected from a halogen or a cyano, nitro, $C_{1-4}$-alkyl, hydroxy, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidinyl, pyrrolidinyl, morpholinyl, $NR_6R_7$, $NHCOR_6$, $COR_6$, $CO_2R_6$, $SO_2R_6$, —O—($C_{1-3}$-alkylene)-O— and 4-piperazinyl optionally substituted by a $C_{1-3}$-alkyl or by a benzyl;

$R_6$ and $R_7$ represent independently of one another a $C_{1-3}$-alkyl group or a phenyl;

and $R_3$ represents a group of formula $CHR_4CONHR_5$ in which $R_4$ represents a hydrogen or a $C_{1-3}$-alkyl group and $R_5$ represents a hydrogen or a $C_{1-3}$-alkyl, $C_{3-5}$-cycloalkyl or $C_{3-7}$-cycloalkyl-$C_{1-6}$-alkylene group, or a pharmaceutically acceptable salt thereof.

6. A process for preparing a compound of formula (I) according to claim 1, comprising reacting the carbamate ester of formula (Ia)

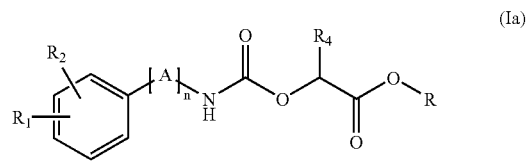

(Ia)

in which A, n, $R_1$, $R_2$ and $R_4$ are as defined for the formula (I) according to claim 1 and R represents a methyl or ethyl group said reacting is performed with an amine of formula $R_5NH_2$ in which $R_5$ is as defined for formula (I) according to claim 1.

7. The process for preparing a compound of formula (I) according to claim 1, comprising reacting the oxazolidinedione of formula (V)

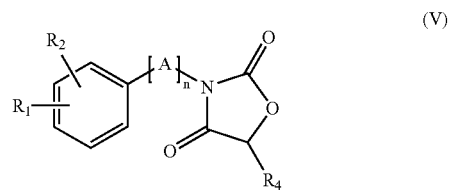

(V)

in which A, n, $R_1$, $R_2$ and $R_4$ are as defined for the formula (I) according to claim 1, said reacting is performed with an amine of formula $R_5NH_2$ in which $R_5$ is as defined for the formula (I) according to claim 1.

8. A pharmaceutical composition comprising a compound of formula (I) as recited in claim 1 or a pharmaceutically acceptable salt thereof in combination with one or more pharmaceutically acceptable excipients.

9. A compound selected from the group consisting of:

2-amino-2-oxoethyl 1-(4'-fluoro-1,1'-biphenyl-4-yl)cyclopropylmethylcarbamate and 2-(methylamino)-2-oxoethyl 1-(4'-fluoro-1,1'-biphenyl-4-yl)cyclopropylmethylcarbamate.

* * * * *

UNITED STATES PATENT AND TRADEMARK OFFICE
CERTIFICATE OF CORRECTION

PATENT NO. : 7,632,850 B2 Page 1 of 1
APPLICATION NO. : 11/186242
DATED : December 15, 2009
INVENTOR(S) : Abouabdellah et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1126 days.

Signed and Sealed this

Second Day of November, 2010

David J. Kappos
*Director of the United States Patent and Trademark Office*

UNITED STATES PATENT AND TRADEMARK OFFICE
CERTIFICATE OF CORRECTION

PATENT NO.         : 7,632,850 B2
APPLICATION NO.    : 11/186242
DATED              : December 15, 2009
INVENTOR(S)        : Ahmed Abouabdellah et al.

It is certified that error appears in the above-identified patent and that said Letters Patent is hereby corrected as shown below:

In column 3, line 36, delete "z" and insert -- Z --, therefor.

In column 5, line 25, delete "z" and insert -- Z --, therefor.

In column 37, line 60-61, delete "ependyomas," and insert -- ependymomas, --, therefor.

In column 37, line 63, delete "sarcomatoses," and insert -- sarcomatosis, --, therefor.

In column 38, line 66, delete "croscaramellose" and insert -- croscarmellose --, therefor.

In column 39, line 54, in claim 1, delete "1to 5;" and insert -- 1 to 5; --, therefor.

In column 40, line 45, in claim 2, after " 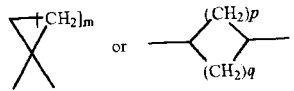 " insert -- ; --.

In column 40, line 53-54, in claim 2, delete "$C_{1-4}$q-alkoxy," and insert -- $C_{1-4}$-alkoxy, --, therefor.

In column 41, line 6, in claim 2, delete "phenylsuiphonyl," and insert -- phenylsulphonyl, --, therefor.

In column 41, line 54, in claim 2, delete "isoquinolinyl" and insert -- isoquinolinyl, --, therefor.

In column 42, line 5, in claim 2, delete "$C_{1-4}$-fluorothioalkyl," and insert -- $C_{1-3}$-fluorothioalkyl, --, therefor.

In column 42, line 22, in claim 3, after "group" insert -- ; --.

In column 42, line 59, in claim 4, delete "1to 5;" and insert -- 1 to 5; --, therefor.

In column 43, line 21, in claim 5, delete "isoquinolinyl" and insert -- isoquinolinyl, --, therefor.

In column 43, line 23, in claim 5, delete "oxadiazolyl" and insert -- oxadiazolyl, --, therefor.

Signed and Sealed this
Thirtieth Day of August, 2011

David J. Kappos
*Director of the United States Patent and Trademark Office*